(12) United States Patent
Thiele et al.

(10) Patent No.: US 11,542,341 B2
(45) Date of Patent: Jan. 3, 2023

(54) KIT FOR DETECTING CORONARY ARTERY DISEASE COMPRISING AN MAA PROTEIN ADDUCT AND REAGENTS THAT BIND TO ANTIBODIES

(71) Applicant: Board of Regents of the University of Nebraska, Lincoln, NE (US)

(72) Inventors: Geoffrey M. Thiele, Omaha, NE (US); Daniel R. Anderson, Omaha, NE (US); Michael J. Duryee, Omaha, NE (US)

(73) Assignee: Board of Regents of The University Of Nebraska, Lincoln, NE (US)

( * ) Notice: Subject to any disclaimer, the term of this patent is extended or adjusted under 35 U.S.C. 154(b) by 98 days.

(21) Appl. No.: 16/782,015

(22) Filed: Feb. 4, 2020

(65) Prior Publication Data
US 2020/0249224 A1 Aug. 6, 2020

Related U.S. Application Data

(63) Continuation of application No. 15/900,680, filed on Feb. 20, 2018, now Pat. No. 10,591,468, which is a continuation of application No. 14/004,514, filed as application No. PCT/US2012/028813 on Mar. 12, 2012, now abandoned.

(60) Provisional application No. 61/451,729, filed on Mar. 11, 2011.

(51) Int. Cl.
| | |
|---|---|
| *C07K 16/42* | (2006.01) |
| *C07K 14/47* | (2006.01) |
| *G01N 33/564* | (2006.01) |
| *G01N 33/68* | (2006.01) |
| *A61P 9/10* | (2006.01) |
| *C07K 16/06* | (2006.01) |
| *C07K 16/18* | (2006.01) |
| *A61K 49/00* | (2006.01) |
| *G01N 33/53* | (2006.01) |

(52) U.S. Cl.
CPC .............. *C07K 16/42* (2013.01); *C07K 14/47* (2013.01); *G01N 33/564* (2013.01); *G01N 33/686* (2013.01); *G01N 33/6854* (2013.01); *A61K 49/00* (2013.01); *A61P 9/10* (2018.01); *C07K 16/06* (2013.01); *C07K 16/18* (2013.01); *G01N 33/5308* (2013.01); *G01N 2440/10* (2013.01); *G01N 2800/324* (2013.01)

(58) Field of Classification Search
CPC ................................. C07K 16/18; C07K 16/42
See application file for complete search history.

(56) References Cited

U.S. PATENT DOCUMENTS

| | | | |
|---|---|---|---|
| 5,939,535 A | 8/1999 | Thiele et al. | |
| 7,713,705 B2 | 5/2010 | Buechler et al. | |
| 7,935,498 B2 | 5/2011 | Christie | |
| 10,591,468 B2 | 3/2020 | Thiele et al. | |
| 2003/0100036 A1 | 5/2003 | Vojdani | |
| 2006/0127955 A1* | 6/2006 | Rothenberg | ............ A61P 15/00 435/7.2 |
| 2014/0170068 A1 | 6/2014 | Thiele et al. | |
| 2018/0313826 A1 | 11/2018 | Thiele et al. | |

FOREIGN PATENT DOCUMENTS

| | | |
|---|---|---|
| CN | 1751128 A | 3/2006 |
| WO | WO 1997/015599 | 5/1997 |

OTHER PUBLICATIONS

PCT International Search Report and Written Opinion dated Apr. 18, 2012 issued in PCT/US2012/028813.
PCT International Preliminary Report on Patentability dated Sep. 17, 2013 issued inPCT/US2012/028813.
Australian Office Action dated Dec. 1, 2015 issued in AU2012229156.
Chinese Office Action dated Oct. 20, 2014 issued in CN201280022809.3.
Chinese Second Office Action dated Jun. 10, 2015 issued in CN201280022809.3.
Chinese Third Office Action dated Feb. 3, 2016 issued in CN201280022809.3.
Chinese Office Action dated Sep. 27, 2016 issued in CN201510867029.4.
European Office Action dated Aug. 18, 2016 issued in EP12710424.8.
European Second Office Action dated Sep. 29, 2015 issued in EP12710424.8.
European Third Office Action dated May 3, 2017 issued in EP12710424.8.
U.S. Office Action dated Feb. 11, 2015 issued in U.S. Appl. No. 14/004,514.
U.S. Final Office Action dated Sep. 30, 2015 issued in U.S. Appl. No. 14/004,514.
U.S. Office Action dated Feb. 21, 2017 issued in U.S. Appl. No. 14/004,514.
U.S. Final Office Action dated Mar. 21, 2019 issued in U.S. Appl. No. 15/900,680.

(Continued)

*Primary Examiner* — Zachary C Howard
(74) *Attorney, Agent, or Firm* — Tom Hunter; Weaver Austin Villeneuve & Sampson LLP

(57) ABSTRACT

In various embodiments methods are provided for identifying a mammal having an elevated risk for an adverse cardiac event (e.g. an MI) and/or determining the prognosis for the mammal. In certain embodiments the methods comprise determining, or causing to be determined, the presence and/or level of antibodies that bind a malondialdehyde acetaldehyde adduct (MAA adduct) in a biological sample from the mammal, where an elevated level of anti-MAA adduct antibodies, as compared to the level found in a normal healthy mammal is an indicator that that said mammal has one or more atherosclerotic lesions and/or is at elevated risk for a myocardial infarction.

5 Claims, 10 Drawing Sheets

(56) References Cited

OTHER PUBLICATIONS

U.S. Notice of Allowance dated Nov. 6, 2019 issued in U.S. Appl. No. 15/900,680.

Anderson et al. (2014) "Unique Antibody Responses to Malondialdehyde-Acetaldehyde (MAA)-Protein Adducts Predict Coronary Artery Disease" Plos One 9(9): e107440 (10 pages).

Chen et al. (2006) "Measurement of anti-acetaldehyde protein adduct antibody titers in the sera of different people" *Chinese Journal of Clinical Hepatology* 22(4):281-282 [English Abstract].

Duryee et al. (2010) "Malondialdehyde-acetaldehyde adduct is the dominant epitope after MDA modification of proteins in atherosclerosis" *Free Radical Biology and Medicine* 49(10): 1480-1486.

Hill et al. (1998) "Association of malondialdehyde-acetaldehyde (MAA) adducted proteins with atherosclerotic-induced vascular inflammatory injury" *Atherosclerosis*, 141: 107-116.

Maggie et al. (1994) "LDL oxidation in patients with severe carotid atherosclerosis. A study of in vitro and in vivo oxidation markers." *Arteriosclerosis, Thrombosis, and Vascular Biology* 14:1892-1899 doi: 10.1161/01.ATV.14.12.1892.

Rolla et al. (2000) "Detection of Circulating Antibodies Against Malondialdehyde-Acetaldehyde Adducts in Patients With Alcohol-Induced Liver Disease." *Hepatology* 31(4):878-884.

Thiele et al. (2004) "Malondialdehyde-acetaldehyde (MAA) modified proteins induce pro-inflammatory and pro-fibrotic responses by liver endothelial cells" *Comparative Hepatology* 3(Suppl 1):S25 (4 pages).

Tuma et al. (1996) "Acetaldehyde and malondialdehyde react together to generate distinct protein adducts in the liver during long-term ethanol administration" *Hepatology*, 23(4): 872-880.

Yang et al. (2009) "The measurement of circulating antibodies against malondialdehyde-acetaldehyde adducts titers in patients with alcohol induced liver disease" *Chinese Journal of Gastroenterology and Hepatology* 18(2): 117-120 [English Abstract].

\* cited by examiner ns of U.S. Ser. No. 15/900, 680, filed Feb. 20, 2018, which is a continuation of U.S. Ser. No. 14/004,514, filed Dec. 24, 2013, which is a 371 National Phase of PCT/US2012/028813, filed on Mar. 12, 2012, which claims priority to and benefit of U.S. Ser. No. 61/451, 729, filed on Mar. 11, 2011, all of which are incorporated herein by reference in their entirety for all purposes.

KIT FOR DETECTING CORONARY ARTERY DISEASE COMPRISING AN MAA PROTEIN ADDUCT AND REAGENTS THAT BIND TO ANTIBODIES

CROSS-REFERENCE TO RELATED APPLICATIONS

This application is a continuation of U.S. Ser. No. 15/900, 680, filed Feb. 20, 2018, which is a continuation of U.S. Ser. No. 14/004,514, filed Dec. 24, 2013, which is a 371 National Phase of PCT/US2012/028813, filed on Mar. 12, 2012, which claims priority to and benefit of U.S. Ser. No. 61/451, 729, filed on Mar. 11, 2011, all of which are incorporated herein by reference in their entirety for all purposes.

STATEMENT OF GOVERNMENTAL SUPPORT

[Not Applicable]

BACKGROUND

Atherosclerotic sequelae, such as peripheral arterial occlusion disease, coronary artery disease as well as the apoplectic cerebral insultus, are still among the main causes of death in the United States, Europe, and in large parts of Asia. In particular, coronary artery disease (CAD) is the leading cause of mortality in the U.S., and the cause of death for one in 2.7 Americans.

The development of the atherosclerosis is considered to be a chronic progressive inflammation of the arterial vessel wall which is characterized by a complex interaction of growth factors, cytokines and cell interactions. In general, LDLs and other proteins become oxidized, bind and activate endothelial cells and then move into the tissue surrounding the vasculature. Macrophages bind to the activated endothelial cells and infiltrate into the area. Scavenger receptors (SRs) on macrophages and endothelial cells bind and internalize these materials forming "foam cells". Lipid peroxidation occurs and more LDLs and proteins are oxidized that bind to the endothelial macrophages. The expression of endothelial adhesion molecules such as selectins, integrins, ICMA-1, VCAM-1 and platelet-endothelial-cell adhesion molecule-1, and the like, mediate adhesion of monocytes and T-lymphocytes in the lumen and inflammatory cytokines/chemokines (e.g., IL-6, CRP, TNF, IL-1, etc.) are released. Eventually substantial cellular apoptosis/necrosis occurs. The plaque becomes unstable and ultimately the cap is destroyed.

Importantly, 70% of individuals who are 40 years of age and older have CAD, however, it is subclinical with no physical symptoms. As well, there is no currently available non-invasive testing that is able to identify these CAD individuals. Invasive testing (e.g., cardiac catheterization) of these patients to determine the presence of non-obstructive and subclinical CAD is contraindicated. Non-invasive imaging including computed tomography (CT) and magnetic resonance (MR) coronary angiography (CTA and MRA) are not reliable in the detecting these CAD lesions.

SUMMARY

In various embodiments methods of identifying a mammal having an elevated risk for an adverse cardiac event (e.g., myocardial infarction) and/or determining the prognosis for the mammal are provided. In certain embodiments the methods typically comprise determining, or causing to be determined, the presence and/or level of antibodies that bind a malondialdehyde-acetaldehyde adduct (MAA adduct) in a biological sample from the mammal, where an elevated level of the antibodies, as compared to the level found in a normal healthy mammal is an indicator that that the mammal has one or more atherosclerotic lesions. In certain embodiments the method comprises determining, or causing to be determined, the presence and/or level of IgG antibodies that bind the adduct, and/or IgM antibodies that bind the adduct, and/or IgA antibodies that bind the adduct. In certain embodiments an elevated level of IgG antibodies and/or IgM antibodies (as compared to the level(s) found in a normal healthy mammal) is an indicator that that the mammal has one or more atherosclerotic plaques and is at risk for cardiac artery disease. In various embodiments the higher the IgG and/or IgM antibodies the greater the disease severity and/or risk of an adverse event (e.g., a myocardial infarction). In certain embodiments a level of the IgA antibodies elevated as compared to that found in a normal healthy mammal is an indicator that the mammal has stable angina. In certain embodiments a level of the IgA antibodies comparable to that found in a normal healthy mammal associated with elevated IgG and/or IgM is an indicator that the mammal has unstable angina and is at significant risk for a myocardial infarction. In various embodiments (e.g., high IgG and/or IgM and high IgA), the mammal is treated as a subject having elevated risk for an adverse cardiac event and/or as a subject having a stable angina. In certain embodiments (e.g., high IgG and/or IgM and low IgA) the mammal is treated as a subject having an unstable angina and is at significant risk for a myocardial infarction. In certain embodiments the mammal is prescribed an additional test and/or the additional tests are performed. In certain embodiments the additional tests are not measurements of antibodies that bind a MAA adduct. In certain embodiments the additional tests comprise one or more tests selected from the group consisting of blood tests for heart tissue damage or high risk for heart attack, electrocardiogram, stress test, coronary MM, and coronary angiography. In certain embodiments the blood tests include one or more tests selected from the group consisting of troponin I, T-00745, creatine phosphokinase (CPK), and myoglobin. In certain embodiments the stress test comprises one or more tests selected from the group consisting of an exercise tolerance test, a nuclear stress test, and a stress echocardiogram. In certain embodiments, in response to the assay data, the mammal is prescribed a treatment and/or treated or a treatment regimen is altered. In certain embodiments the treatments comprise a change in diet and/or exercise. In certain embodiments the treatment comprises administration of one or more pharmaceuticals (e.g., one or more pharmaceuticals selected from the group consisting of a statin, a beta blocker, nitroglycerin or other nitrate, heparin, angiotensin receptor blockers (ARB), aspirin and other anti-platelets, calcium channel blocker, and Ranolazine). In certain embodiments the treatment is a treatment selected from the group consisting of angioplasty, implantation of a stent, and coronary bypass surgery. In certain embodiments the anti-MAA adduct IgG antibody or anti-MAA-IgM antibody levels and/or a diagnosis based, at least in part, on the levels is recorded in a patient medical record. In certain embodiments the anti-MAA adduct IgA antibody levels and/or a diagnosis based, at least in part, on the levels is recorded in a patient medical record. In certain embodiments the patient medical record is maintained by a laboratory, physician's office, a hospital, a health maintenance organization, an insurance company, or a personal medical record website. In certain embodiments a diagnosis, based at least in part on the anti-MAA adduct IgG antibody level, and/or IgM antibody level, and/or IgA antibody level is recorded on or in a medic alert article selected from a card, worn article, or radiofrequency identification (RFID) tag. In certain embodiments the antibody levels and/or a diagnosis based upon the levels of the antibodies is recorded on a non-transient computer readable medium. In certain embodiments the method additionally comprises informing the subject of a result of anti-MAA adduct antibody and/or of a diagnosis based at least in part on anti-MAA adduct antibody assay. In certain embodiments the antibodies that bind a MAA adduct are detected as part of a differential diagnosis. In certain embodiments the mammal is a non-human mammal and the biological sample is from the non-human mammal. In certain embodiments the mammal is a human and the biological sample is from the human. In certain embodiments the biological sample comprise a sample selected from the group consisting of whole blood, a blood fraction, saliva/oral fluid, urine, a tissue biopsy, pleural fluid, pericardial fluid, cerebral spinal fluid, and peritoneal fluid. In various embodiments an anti-MAA adduct antibody is detected in an assay where the biological sample is fractionated to separate a fraction comprising the antibody from at least one other sample component. In certain embodiments the mammal is a mammal known to have or suspected of having atherosclerosis and/or know to have or suspected of having one or more risk factors for cardiovascular disease. In certain embodiments the mammal has one or more risk factors selected from the group consisting of a familial risk for heart disease, elevated blood pressure, high LDL cholesterol and low HDL cholesterol, high triglycerides, obesity, and diabetes, tobacco use, metabolic syndrome, connective tissue disorder, chronic infections, and inflammatory bowel disease. In certain embodiments IgG antibodies and/or IgM antibodies, and/or IgA antibodies that bind a MAA adduct are detected in an assay where the antibody and/or a complex formed between the antibody and a MAA adduct becomes labeled with a detectable label. In certain embodiments IgG antibodies, and/or IgM antibodies, and/or IgA antibodies that bind a MAA adduct are detected in an assay where the antibodies go from an unbound state to a bound state by forming a complex with another assay component. In certain embodiments IgG antibodies, and/or IgM antibodies, and/or IgA antibodies that bind a MAA adduct are detected in an assay where the antibodies initially present in a soluble phase becomes immobilized on a solid phase. In certain embodiments level of one or more of the IgG antibody, the IgM antibody, and/or the IgA antibody is measured using an assay selected from the group consisting of SDS/PAGE, isoelectric focusing, 2-dimensional gel electrophoresis, a hemagglutination assay, and an immunoassay. In certain embodiments the level of one or more of the IgG antibody, the IgM antibody, and/or the IgA antibody is measured using an ELISA assay. In certain embodiments the immunoassay comprises providing a MAA adduct immobilized on a solid support; contacting the MAA adduct with the biological sample under conditions in which anti-MAA adduct antibodies in the sample are bind MAA adduct forming an adduct/antibody complex; and contacting the complex with detection antibodies that specifically bind IgG antibodies or IgA antibodies, or IgM antibodies, or contacting the complex with a detection reagent that binds any antibody; and detecting and/or quantifying the bound detection antibodies or the bound detection reagent. In certain embodiments the detection antibodies are attached to a detectable label or bound by another antibody attached to a detectable label; and/or the detection reagent is attached to a detectable label and/or the detection reagent is bound by an antibody attached to a detectable label; and the detecting and/or quantifying comprises detecting and/or quantifying the detectable label.

In various embodiments methods of monitoring the progression of atherosclerosis and/or coronary artery disease in a mammal are provided. The method typically comprise determining, or causing to be determined, the presence and/or level of antibodies that bind a malondialdehyde-acetaldehyde adduct (MAA adduct) in a biological sample from the mammal; and comparing the level(s) of the antibodies to levels that have been measured for the mammal at a previous point in time, where an increase in the total level(s) of antibodies that bind the MAA adduct in the biological sample, as compared to the previous determination, is an indicator that atherosclerotic lesions have worsened in the mammal; and a decrease in the total level(s) of antibodies that bind the MAA adduct in the biological sample, as compared to the previous determination, is an indicator that atherosclerotic lesions decreased in the mammal. In certain embodiments the mammal is treated for atherosclerosis, and/or coronary artery disease during the time between the previous point in time and the time the determining or causing to be determined and an increase in the total level(s) of antibodies that bind the MAA adduct in the biological sample, as compared to the previous determination, is an indicator the treatment has limited or no efficacy and that plaques have worsened in the mammal; and a decrease in the total level(s) of antibodies that bind the MAA adduct in the biological sample, as compared to the previous determination, is an indicator that the treatment has at least some efficacy and that plaques decreased in the mammal. In certain embodiments the method comprises determining, or causing to be determined, the presence and/or level of IgG antibodies that bind the adduct. In certain embodiments the method comprises determining, or causing to be determined, the presence and/or level of IgM antibodies that bind the adduct. In certain embodiments the method comprises determining, or causing to be determined, the presence and/or level of IgA antibodies that bind the adduct. In certain embodiments an increase in the total level(s) of antibodies that bind the MAA adduct in the biological sample and/or a class switching from IgM to IgG antibodies, as compared to the previous determination, is an indicator that atherosclerotic lesions (plaques) have worsened in the mammal; and a decrease in the total level(s) of antibodies that bind the MAA adduct in the biological sample and/or a class switching from IgG to IgM antibodies, as compared to the previous determination, is an indicator that atherosclerotic lesions (plaques) have decreased in the mammal. In certain embodiments an increase in IgA antibodies, as compared to the previous determination is an indicator that atherosclerotic lesions in the mammal are become more stable, and/or that the treatment is at least partially increasing the stability of atherosclerotic lesions in the mammal. In certain embodiments the treatment comprises one or more modalities selected from the group consisting of the mammal, a change in diet, an increase in exercise, prescription/administration of a statin, prescription/administration of a beta blocker, prescription/administration of a calcium channel blocker. In certain embodiments if the measurements provide an indicator that the treatment has limited or no efficacy and/or that lesions have worsened in the mammal the mammal is prescribed an additional test and/or additional tests are performed. In certain embodiments the additional tests are not measurements of antibodies that bind a MAA adduct. In certain embodiments the additional tests comprise one or more tests selected from the group consisting of blood tests for heart tissue damage or high risk for heart attack, electrocardiogram, stress test, coronary MRI, and coronary angiography. In certain embodiments the blood tests include one or more tests selected from the group consisting of troponin I, T-00745, creatine phosphokinase (CPK), and myoglobin. In certain embodiments the stress test comprises one or more tests selected from the group consisting of an exercise tolerance test, a nuclear stress test, and a stress echocardiogram. In certain embodiments if the measurements provide an indicator that the treatment has limited or no efficacy and/or that lesions have worsened in the mammal the mammal is prescribed and/or treated using a new treatment, a different treatment, or an additional treatment. In certain embodiments the treatment comprises administration of a pharmaceutical (e.g., one or more pharmaceuticals selected from the group consisting of a statin, a beta blocker, nitroglycerin or other nitrate, heparin, ACE inhibitor, angiotensin receptor blockers (ARB), aspirin and other anti-platelets, calcium channel blocker, and Ranolazine). In certain embodiments the treatment is a treatment selected from the group consisting of angioplasty, implantation of a stent, and coronary bypass surgery. In certain embodiments the mammal is a non-human mammal and the biological sample is from the non-human mammal or the mammal is a human and the biological sample is from the human. In certain embodiments the biological sample comprise a sample selected from the group consisting of whole blood, a blood fraction, plasma, serum, interstitial fluid, saliva/oral fluid, urine, a tissue biopsy, pleural fluid, pericardial fluid, cerebral spinal fluid, and peritoneal fluid. In certain embodiments an anti-MAA adduct antibody is detected in an assay where the biological sample is fractionated to separate a fraction comprising the antibody from at least one other sample component. In certain embodiments the mammal is a mammal known to have or suspected of having atherosclerosis. In certain embodiments the mammal has one or more risk factors selected from the group consisting of a familial risk for heart disease, elevated blood pressure, high LDL cholesterol and low HDL cholesterol, high triglycerides, obesity, and diabetes, tobacco use, metabolic syndrome, connective tissue disorder, chronic infections, and inflammatory bowel disease.

In various embodiments a method of treating a mammal is provided where the method comprises receiving measurements of the presence and/or level of antibodies that bind a malondialdehyde acetaldehyde adduct (MAA adduct) in a biological sample from the mammal, where an elevated level of the antibodies, as compared to the level found in a normal healthy mammal is an indicator that that the mammal has one or more atherosclerotic lesions; and when the antibodies show an elevated level providing or causing to be provided additional tests relevant to atherosclerosis and/or providing or causing to be provided additional treatments relevant to atherosclerosis to the mammal. In certain embodiments the method comprises receiving a measurement of the presence and/or level of IgG antibodies that bind the adduct. In certain embodiments the method comprises receiving a measurement of the presence and/or level of IgM antibodies that bind the adduct. In certain embodiments the method where the method comprises receiving a measurement of the presence and/or level of IgA antibodies that bind the adduct. In certain embodiments the receiving measurements comprise retrieving and/or viewing the measurements in a patient medical record. In certain embodiments the receiving measurements comprise retrieving and/or viewing the measurements in a report from a diagnostic laboratory. In certain embodiments the receiving measurements comprise ordering the assay and receiving the assay results. In various embodiments a level of the IgA antibodies elevated (e.g. a statistically significant elevation at at least a 95% confidence level, preferably at least a 98% confidence level, more preferably at at least a 99% confidence level using any appropriate parametric or non-parametric test) as compared to that found in a normal healthy mammal is an indicator that the mammal has stable angina, and the mammal is further tested and/or treated as a subject having or at risk for a stable angina. In various embodiments a level of the IgA antibodies comparable to that found in a normal healthy mammal is an indicator that the mammal has unstable angina and is at significant risk for a myocardial infarction, and the mammal is further tested and/or treated as a subject having or at risk for an unstable angina and and/or a myocardial infarction. In certain embodiments the mammal is prescribed an additional test and/or the additional tests are performed. In certain embodiments the additional tests are not measurements of antibodies that bind a MAA adduct. In certain embodiments the additional tests comprise one or more tests selected from the group consisting of blood tests for heart tissue damage or high risk for heart attack, electrocardiogram, stress test, coronary MM, and coronary angiography. In certain embodiments the blood tests include one or more tests selected from the group consisting of troponin I, T-00745, creatine phosphokinase (CPK), and myoglobin. In certain embodiments the stress test comprises one or more tests selected from the group consisting of an exercise tolerance test, a nuclear stress test, and a stress echocardiogram. In certain embodiments the mammal is prescribed a treatment and/or treated. In certain embodiments the treatment comprises administration of a pharmaceutical (e.g., one or more pharmaceuticals selected from the group consisting of a statin, a beta blocker, nitroglycerin or other nitrate, heparin, ACE inhibitor, calcium channel blocker, and Ranolazine). In certain embodiments the treatment is a treatment selected from the group consisting of angioplasty, implantation of a stent, and coronary bypass surgery. In certain embodiments the mammal is a non-human mammal and the biological sample is from the non-human mammal or the mammal is a human and the biological sample is from the human. In certain embodiments the biological sample comprise a sample selected from the group consisting of whole blood, a blood fraction, plasma, serum, interstitial fluid, saliva/oral fluid, urine, a tissue biopsy, pleural fluid, pericardial fluid, cerebral spinal fluid, and peritoneal fluid. In certain embodiments an anti-MAA adduct antibody is detected in an assay where the biological sample is fractionated to separate a fraction comprising the antibody from at least one other sample component. In certain embodiments the mammal is a mammal known to have or suspected of having atherosclerosis (and/or known to have or suspected of having one or more risk factors for atherosclerosis). In certain embodiments the mammal has one or more risk factors selected from the group consisting of a familial risk for heart disease, elevated blood pressure, high LDL cholesterol and low HDL cholesterol, high triglycerides, obesity, and diabetes, tobacco use, metabolic syndrome, connective tissue disorder, chronic infections, and inflammatory bowel disease. In certain embodiments the measurements of IgG antibodies and/or IgM antibodies, and/or IgA antibodies that bind a MAA adduct are determined in an assay where the antibody and/or a complex formed between the antibody and a MAA adduct becomes labeled with a detectable label. In certain embodiments the measurements of IgG antibodies, and/or IgM antibodies, and/or IgA antibodies that bind a MAA adduct are determined in an assay where the antibodies go from an unbound state to a bound state by forming a complex with another assay component. In certain embodiments the measurements of IgG antibodies, and/or IgM antibodies, and/or IgA antibodies that bind a MAA adduct are determined in an assay where the antibodies initially present in a soluble phase becomes immobilized on a solid phase. In certain embodiments the level of one or more of the IgG antibody, the IgM antibody, and/or the IgA antibody is measured using an assay selected from the group consisting of SDS/PAGE, isoelectric focusing, 2-dimensional gel electrophoresis, a hemagglutination assay, and an immunoassay. In certain embodiments the IgG antibody, the IgM antibody, and/or the IgA antibody is measured using an ELISA assay. In various embodiments the immunoassay comprises providing a MAA adduct immobilized on a solid support; contacting the MAA adduct with the biological sample under conditions in which anti-MAA adduct antibodies in the sample are bind MAA adduct forming an adduct/antibody complex; and contacting the complex with detection antibodies that specifically bind IgG antibodies or IgA antibodies, or IgM antibodies, or contacting the complex with a detection reagent that binds any antibody; and detecting and/or quantifying the bound detection antibodies or the bound detection reagent. In certain embodiments the detection antibodies are attached to a detectable label or bound by another antibody attached to a detectable label; and/or the detection reagent is attached to a detectable label and/or the detection reagent is bound by an antibody attached to a detectable label; and the detecting and/or quantifying comprises detecting and/or quantifying the detectable label.

In certain embodiments kits for evaluating the presence and/or prognosis for atherosclerosis (and/or coronary artery disease) in a mammal, are provided. In certain embodiments the kits comprise packaging containing a MAA protein adduct; and a first reagent that specifically binds to IgG antibodies bound to the MAA protein adduct and/or a second reagent that specifically binds to IgM antibodies bound to the MAA protein adduct. In certain embodiments the kit further comprises a third reagent that specifically binds to IgA antibodies bound to the MAA protein adduct. In certain embodiments the first reagent comprises an antibody that binds to an IgG antibody bound to the MAA protein adduct. In certain embodiments the second reagent comprises an antibody that binds to an IgM antibody bound to the MAA protein adduct. In certain embodiments the third reagent comprises an antibody that binds to an IgA antibody bound to the MAA protein adduct. In certain embodiments the MAA protein adduct is provided immobilized on a solid support. In certain embodiments the solid support comprises a material selected from the group consisting of a plastic, glass, quartz, a gel, and a metal. In certain embodiments the solid support is selected from the group consisting of a particle, a test strip, a microtiter plate, an ELISA plate, and a microfluidic channel or chamber. In certain embodiments the kit further comprises instructional materials that teach the use of measurement of antibodies against a MAA adduct to evaluate the risk for an adverse cardiac event, and/or to determine the prognosis of a mammal, and/or to evaluate the progression of atherosclerosis in a mammal, and/or to evaluate a treatment regimen. In certain embodiments the kit is for use in evaluating the risk for an adverse cardiac event, and/or determining the prognosis of a mammal, and/or to evaluating the progression of atherosclerosis in a mammal, and/or to evaluating a treatment regimen.

In various embodiments methods of treating a mammal, are provided where the methods comprise administering (or causing to be administered) to the mammal a composition comprising an antibody that specifically binds a MAA adduct attached to a detectable label or capable of being selectively bound by a detectable label; and detecting the localization of the label within the mammal's vasculature where the localization indicates a potentially unstable plaque. In certain embodiments the method further comprises treating the potentially unstable plaque. In certain embodiments the treating comprises performing angioplasty to the region where the plaque is localized and/or inserting a stent in the region where the plaque is localized.

Definitions

The term "biological sample" or "test sample" refers to sample is a sample of biological tissue, cells, or fluid that, in a healthy and/or pathological state, contains an analyte that is to be detected, e.g., an antibody reactive to a MAA protein adduct (e.g., an anti-MAA adduct IgG, IgA, IgM, etc.). Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is typically taken from a human subject (e.g., patient), the assays can be used to detect anti-MAA adduct antibodies in samples from any mammal, such as dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, inactivation of interfering components, the addition of reagents, lysing, etc. If such methods of pretreatment are employed with respect to the sample, such pretreatment methods are typically such that the analyte of interest (e.g., anti-MAA adduct antibodies) remains in the test sample, preferably at a concentration proportional to that in an untreated test sample (e.g., namely, a sample that is not subjected to any such pretreatment method(s)). Such "treated" or "processed" samples are still considered to be biological samples with respect to the methods described herein.

The term "blood" includes whole blood, or blood fractions such as serum or plasma.

By "diagnostic test" is meant any kind of medical test performed to aid in the diagnosis or detection of disease and/or pathology.

An antibody when used with respect to an analyte that is to be detected in a diagnostic/prognostic assay as described herein (e.g., an anti-MAA protein adduct antibody) refers to an endogenous (endogenously generated antibody). The antibody typically comprises one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An antibody when used with respect to a targeting moiety used for the detection of a particular antigen (e.g., MAA adduct) refers to an a full (intact immunoglobulin) or as any of a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), e.g., single chain Fv antibodies (sFv or scFv) in which a variable heavy and a variable light chain are joined together (directly or through a peptide linker) to form a continuous polypeptide. The single chain Fv antibody is typically a covalently linked $V_H$-$V_L$ heterodimer which may be expressed from a nucleic acid including $V_H$- and $V_L$-encoding sequences either joined directly or joined by a peptide-encoding linker (see, e.g., Huston, et al. (1988) *Proc. Nat. Acad. Sci. USA,* 85: 5879-5883).

An "MAA adduct" refers to any macromolecule modified with the MAA moiety as previously described (see, e.g., Hill et al. (1998) Atherosclerosis, 141: 107-116, U.S. Pat. No. 5,939,535, and the like). An "MAA protein adduct" refers to a protein modified with the MAA moiety.

An "anti-MAA adduct antibody" or "anti-MAA protein adduct antibody" refers to an antibody that specifically binds to (e.g., is reactive with) a MAA protein adduct. The MAA protein adduct can be one that is naturally occurring in a mammal, or one that is synthetically produced.

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. Cardiovascular disease includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the ruptures of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease or atherosclerosis. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

A "risk factor" is a factor identified to be associated with an increased risk. A risk factor for a cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include, but are not limited to smoking, adverse lipid profiles, elevated lipids or cholesterol, diabetes, hypertension, hypercoagulable states, elevated homocysteine levels, and lack of exercise. Carrying a particular polymorphic allele can be a risk factor for a particular cardiovascular disorder, and can be associated with an increased risk of a particular disorder.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). Preferably, the subject is a human.

When it is said that the presence or level of a particular marker (e.g., MAA adduct and/or anti-MAA adduct antibody) is an "indicator" of a particular pathology or prognosis it is not intended to suggest that the presence or level of the marker is dispositive for that pathology or prognosis. Rather the indicator is intended to be used in the context of other information (e.g., in the context of a differential diagnosis) to inform further testing and/or evaluation, and/or lifestyle/behavioral changes, and/or to inform further treatment or alteration in treatment regimen.

The phrase "receiving measurements" (e.g., of the presence and/or level of antibodies that bind a malondialdehyde acetaldehyde adduct (MAA adduct)) indicates that the person receiving such measurements obtains the measurements provided by another source, e.g., by reviewing a medical record, provided by a report from a testing laboratory, by a patient/patient history, and the like. In certain embodiments the measurements are received as a consequence of a test ordered by the receiver (e.g., physician). In certain embodiments the measurements can be made by the receiver.

The phrase "cause to be administered" refers to the actions taken typically by a medical professional (e.g., a physician), or a person controlling medical care of a subject, that control and/or permit the administration of the agent(s) at issue to the subject. Causing to be administered can involve diagnosis and/or determination of an appropriate therapeutic or prophylactic regimen, and/or prescribing particular agent(s) for a subject. Such prescribing can include, for example, drafting a prescription form, annotating a medical record, and the like.

The term "elevated" when used with reference to a parameter (e.g., antibody level) indicates that the parameter falls within a range that would be recognized as elevated with respect to a reference value (or reference values) by one of ordinary skill in the art. In certain embodiments the reference value can be a value determined for the subject at a previous point in time. In certain embodiments the reference value(s) can be values know or determined for a particular population or subpopulation (e.g., a subpopulation characterized by one or more factors selected from the group consisting of gender, age, ethnicity, weight, health status, and the like). In certain embodiments a parameter is identified as elevated if it falls in a top 25 percentile, or a top 10 percentile, or a top 5 percentile, or a top 2 percentile, or a top 1 percentile of the value for a particular reference population. In certain embodiments the parameter is identified as elevated when the level is a statistically significant elevation at ≥95% confidence level, preferably at ≥98% confidence level, more preferably at ≥99% confidence level using any appropriate parametric (e.g., ANOVA, t-test, and the like) or non-parametric test.

DETAILED DESCRIPTION

Figure 1:
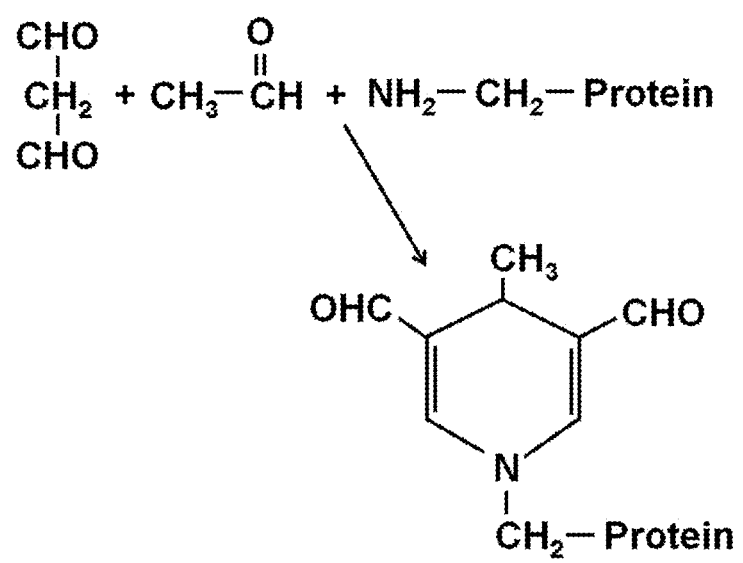
FIG. 1 illustrates a mechanism for the formation of a malondialdehyde/acetaldehyde adduct (MAA).
Figure 2:
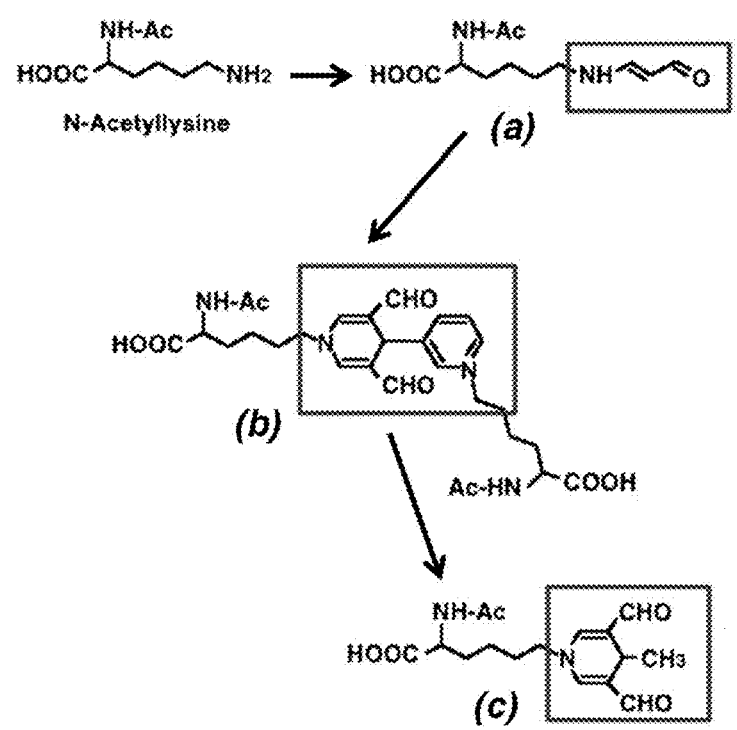
FIG. 2 illustrates a second mechanism for the formation of a malondialdehyde/acetaldehyde adduct (MAA).

It is demonstrated herein that modified proteins (in particular malondialdehyde/acetaldehyde adducts (MAA adducts)) are associated with coronary artery disease (CAD), and believed more generally to be associated with the progression of atherosclerosis. Without being bound by a particular theory, it is believed that MAA adducts are formed under oxidative stress by at least two mechanisms. In one mechanism illustrated schematically in FIG. 1, malondialdehyde (MDA) is at high concentrations. Some malondialdehyde degrades to form acetaldehyde (AA). Two molecules bind to an amino group on a protein substrate that may be available (e.g., LDL), and one molecule of acetaldehyde "cements" the product that is formed. In a second mechanism, illustrated schematically in FIG. 2 One molecule of MDA binds to the amino group of the protein substrate (illustrated in the figure as N-acetyllysine) forming Na-acetyl-N 1-(2-propenal)lysine (a). Two molecules of the product in (a) combined through the MDA modified ends of the molecules (b) forming Na-acetyl-N 1-lysyl-3,5-diformyl-2,6-dihydropyridin-4-yl-pyridinium derivative. A condensation reaction occurs resulting in the formation of the MAA adduct (c), in this case Na-acetyl-N 1-lysyl-4-methyl-2,6-dihydropyridine-3,5-dicarbaldehyde derivative.

Oxidized proteins have been implicated in the development and progression of atherosclerosis. Malondialdehyde/Acetaldehyde (MAA) modified LDLs are highly oxidized and a dominate epitope formed following the modification of proteins with malondialdehyde.

MAA modified proteins also bind scavenger receptors on endothelial cells and macrophages and promote the release of pro-inflammatory cytokines and thus appear to be implicated in the progression of atherosclerosis, and in particular, plaque formation.

Importantly, MAA-modification appears to result in an immune response with antibody production which, as described herein is also associated with the progression and exacerbation of disease (e.g., atherosclerosis, more particularly cardiac artery disease). The mechanism(s) by which MAA-modification and/or antibody production exacerbates disease is not fully understood. However, the presence of antibodies to MAA-modified proteins details not only the presence of CAD, but also the nature of CAD progression.

In particular it was a surprising discovery that anti-MAA adduct antibody titers provide a measure of the severity/risk of cardiac artery disease with increased levels of anti-MAA adduct antibody indicating an increased level of plaque load and/or plaque severity.

Without being bound to a particular theory it is believed that in the progression of atherosclerosis and cardiac artery disease, a site of inflammation is set up where oxidized proteins and LDL bind, internalize and initiate pro-inflammatory responses. Some of the oxLDL and MAA modified proteins are released from the site and migrate to the immune system to initiate immune responses in a load dependent process. Antibody is initiated that correlates with the development of an atherosclerotic plaque as well as its progression. The more antibody to MAA, the greater the chance the plaque is unstable. As the oxLDL and adducted proteins accumulate, more inflammatory cells infiltrate and the plaque grows causing angina. Eventually, the inflammation becomes overwhelming causing thinning of the fibrous plaque cap (due to cytokines and immune reactions), and antibody concentrations increase due to leaky membranes and in response to the leaked modified macromolecules. Eventually the plaque ruptures causes the release of large amounts of oxLDL and MAA-modified proteins that bind the circulating antibody resulting in decreased antibody concentrations.

It was a further surprising discovery that anti-MAA adduct antibody isotypes provide further diagnostic/prognostic information. Specifically, the isotype pattern of the antibodies differentiates the nature of atherosclerotic lesions and allows the identification of patients who are: 1) expected to have an acute myocardial infarction or a heart attack (High IgG, Low IgA), and 2) those that progress in a stable fashion without a heart attack (Low IgG, High IgA).

Without being bound to a particular theory, it is believed that a site of inflammation is set up where oxidized proteins and LDL bind, internalize and initiate pro-inflammatory responses as described above. Some of the oxLDL and MAA modified proteins are released from the site and migrate to the immune system to initiate immune responses in a load-dependent process, resulting in the production of IgM antibodies. As the oxLDL and adducted proteins accumulate, more inflammatory cells infiltrate and the plaque grows causing angina. Eventually, the inflammation becomes overwhelming the IgM antibody is class switched to the more pathogenic IgG antibody that aids in the thinning of the fibrous plaque cap (due to cytokines and immune reactions), and antibody concentrations increase due to leaky membranes and in response to the increased levels of leaked modified macromolecules. Eventually the plaque ruptures causes the release of large amounts of oxLDL and MAA modified proteins and acute myocardial infarction.

Alternatively, in patients with stable CAD, the oxLDL and adducted proteins accumulate on the adventitial side of the cap (not in the lumen of the vasculature) and the inflammatory response is decreased. The cytokines released result in an IgA response that is less pathogenic and the fibrous plaque cap is left intact, resulting in a stable CAD.

Thus analysis of the antibody isotypes of anti-MAA adduct antibodies in the subject provides an indication of the severity/prognosis of the pathology.

Moreover as atherosclerosis represents a progressive continuum of pathology, it is believed that the anti-MAA adduct antibodies more generally provide an indicator of the severity/progression of the atherosclerotic process and cardiovascular disease.

The ability to predict the presence and nature of progression (e.g., stable vs. unstable) of CAD allows identification of patients prior to the typical clinical presentation of disease (e.g., myocardial infarction). This insight permits identification of patients who need treatment with medication such as cholesterol lowering medication (e.g. statins), non-invasive cardiac stress examination (e.g., nuclear studies, stress echocardiograms, CTA, MRA) and/or invasive cardiac examination (e.g., cardiac catheterizations). With this tool it is possible to define patients who are at risk for the development and/or progression of CAD at a much earlier time point in the disease process. With this knowledge patients can be selected for treatment which is appropriately aggressive to prevent the progression, and prevent or delay the heart attack and the associated morbidity and mortality of coronary heart disease. Overall, a more appropriately refined medical testing and treatment strategy is expected to not only allow appropriate earlier treatment, but also decrease the utilization and over-utilization of other non-invasive and invasive testing.

Diagnostic/Prognostic Assays.

Accordingly, in certain embodiments, assays using detection/quantification of anti-MAA adduct antibodies are provided for identifying a mammal having an elevated risk for an adverse cardiac event and/or determining the prognosis for the mammal. The methods typically involve determining, or causing to be determined, the presence and/or level of antibodies that bind a malondialdehyde acetaldehyde adduct (MAA adduct) in a biological sample from said mammal, where an elevated level of anti-MAA adduct antibodies, as compared to the level found in a normal healthy mammal is an indicator that that the mammal has one or more atherosclerotic plaques. In certain embodiments the total anti-MAA adduct antibody level is determined and higher antibody levels indicate greater plaque load and/or associated angina and/or greater risk of an unstable plaque and therefore risk of an adverse cardiac event (e.g., myocardial infarction, cardiac ischemia, etc.).

In certain embodiments levels of different anti-MAA adduct antibody isotypes are identified. In such instances an increasing total antibody titer indicates greater disease severity as explained above. However, antibody class switching from IgM to IgG (e.g., as evidenced by an increase in IgG versus IgM antibodies) indicates increased risk for unstable plaque. Moreover, high IgG and low IgA is an indicator that the subject is expected to have an acute myocardial infarction or a heart attack, while low IgG and high IgA is an indicator that plaque formation may progress in a stable fashion without a heart attack.

These methods can also be used to monitor disease progression in a subject and/or to evaluate a treatment regimen. Such methods can involve determining, or causing to be determined, the presence and/or level of antibodies that bind a malondialdehyde acetaldehyde adduct (MAA adduct) in a biological sample from the mammal; and comparing the level(s) of anti-MAA adduct antibodies to levels that have been measured for said mammal at a previous point in time, where an increase in the total level(s) of antibodies that bind MAA adduct in the biological sample, as compared to the previous determination, is an indicator that atherosclerotic plaques have worsened in said mammal; and a decrease in the total level(s) of antibodies that bind said MAA adduct in said biological sample, as compared to the previous determination, is an indicator that atherosclerotic plaques have decreased in mammal. As discussed herein, decreased antibody levels can be an indicator of an acute cardiac event (e.g., plaque rupture) which may result in the release of modified proteins and thus a decrease in antibody levels. The outcomes can be distinguished by consideration of other factors in a differential diagnosis when associated with other biomarkers (e.g., elevated Troponin I, CPK, LDL or AST) indicative of tissue injury.

Again, in certain embodiments levels of different anti-MAA adduct antibody isotypes are identified. In such instances antibody class switching from IgM to IgG (e.g., as evidenced by an increase in IgG versus IgM antibodies) indicates increased risk while a decrease in IgG versus IgM can be an indicator that the subject is improving. Similarly, an increase in IgG and/or a decrease in IgA can be an indicator that the subject's risk is increasing, while a decrease in IgG and/or an in increase in IgA can be an indicator that the subject is progressing in a more stable matter.

There the subject is treated between the first and second measurement of anti-MAA adduct antibodies the changes in antibody levels as described above provides a measurement of treatment efficacy. Where treatment appears in effective of little efficacy a different treatment regimen (e.g., a more aggressive treatment regimen) can be implemented.

In certain embodiments the diagnostic/prognostic methods described herein can be incorporated into a method of treatment. For example, in certain embodiments, the method can involve receiving measurements of the presence and/or level of antibodies that bind a malondialdehyde acetaldehyde adduct (MAA adduct) in a biological sample from the mammal, where an elevated level of the antibodies, as compared to the level found in a normal healthy mammal is an indicator that that the mammal has one or more atherosclerotic plaques; and when the antibodies show an elevated level, providing or causing to be provided additional tests relevant to atherosclerosis and/or providing or causing to be provided additional treatments relevant to atherosclerosis to the mammal.

Again, in certain embodiments levels of different anti-MAA adduct antibody isotypes are identified. In such instances antibody class switching from IgM to IgG (e.g., as evidenced by an increase in IgG versus IgM antibodies) indicates increased risk and perhaps additional testing and/or a more aggressive treatment regimen, while a decrease in IgG versus IgM can be an indicator that the subject is improving and a less aggressive treatment regimen is warranted or the existing treatment regimen should be maintained. Similarly, an increase in IgG and/or a decrease in IgA can be an indicator that the subject's risk is increasing warranting more testing and/or a more aggressive treatment, while a decrease in IgG and/or an in increase in IgA can be an indicator that the subject is progressing in a more stable matter and perhaps the existing treatment regimen can be simply maintained or the treatment can be reduced.

As indicated above positive results in the various assays described herein can provide an indication of the presence, severity, or increasing severity of an underlying pathology (e.g., atherosclerosis/cardiovascular disease). In certain embodiments the presence of positive results may indicate/warrant further testing. Additional tests can include, but need not be limited to one or more tests selected from the group consisting of HDL/LDL ratio, total cholesterol, triglyceride levels, lipoprotein associated phospholipase $A_2$ ($LpPLA_2$), homocystein, C-reactive protein (CRP), HSP70, high density lipoprotein (HDL), TNFα, HSP60, troponin I, T-00745, creatine phosphokinase (CPK), and myoglobin, stress tests (e.g., exercise tolerance test, nuclear stress test, a stress echocardiogram, etc.), imaging studies (e.g., cardiac NMR, angiogram, etc.), and the like.

As indicated above positive results in the various assays described herein can provide an indication of the presence, severity, or increasing severity of an underlying pathology (e.g., atherosclerosis/cardiovascular disease). In certain embodiments the presence of positive results may indicate/warrant further an alteration, implementation, or increase in treatment regimen. In certain embodiments the treatment regimen may comprise behavioral modification (e.g., changes in diet and exercise), administration of a one or more pharmaceuticals (e.g., one or more agents selected from the group consisting of a statin, a beta blocker, nitroglycerin or other nitrate, heparin, ACE inhibitor, calcium channel blocker, Ranolazine, and the like), and/or one or more procedures (e.g., angioplasty, implantation of a stent, coronary bypass surgery, vascular graft, and the like).

As indicated above, in various embodiments, antibodies reactive to a MAA protein adduct (e.g., anti-MAA adduct IgG, IgM, IgA, etc.) are measured to provide an indication of the presence and/or severity of plaque formation in a subject and/or the prognosis for such plaques. In certain embodiments the antibody levels are evaluated with respect to comparable antibody levels found in a normal healthy subject. In certain embodiments the antibody levels are evaluated with respect to the antibody levels determined in the subject at a previous point in time.

In any given population, levels of antibodies with reactivity to a MAA adduct are likely to vary. In certain embodiments the level of antibodies with reactivity to a MAA adduct conjugate determined for any given individual may be categorized as high or low by reference to the range observed in the wider population. For example, a level of such antibodies below a particular percentile value determined with reference to the wider population may be categorized as a low level. In certain embodiments, a low level may correspond to a value below the 25th percentile, or below the 20th, 10th or 5th percentile. In certain embodiments a high level may correspond to a value of above the 5th, 10th, 20th, or 25th percentile, for example.

As will be apparent, the diagnostic and prognostic methods provided by the present invention require a degree of quantification to determine either, the amount of anti-MAA adduct antibody that is diagnostic or prognostic of a pathology. In certain embodiments such quantification can be determined by the inclusion of appropriate reference samples in the assays described herein, wherein said reference samples are synthetic samples (e.g., by providing known quantities of anti-MAA adduct antibody in a buffer), and/or derived from healthy or normal individuals.

In one embodiment, the reference sample comprises a biological sample (for example plasma, serum, whole blood, sputum, saliva, etc.) derived from the same subject when the individual was not suffering from or manifesting any clinical symptoms and/or risk factors. In another embodiment, the reference sample comprises a biological sample derived from a normal healthy individual.

Accordingly, a reference sample and a test (e.g., patient) sample are both processed, analyzed or assayed and data obtained for a reference sample and a test sample are compared. In one embodiment, a reference sample and a test sample are processed, analyzed or assayed at the same time. In another embodiment, a reference sample and a test sample are processed, analyzed or assayed at different times.

Alternatively, or in addition, the data for the test sample is compared to a data for a reference sample derived from an established data set that has been previously generated. Accordingly, in one embodiment, a reference sample comprises previously determined values or ranges (e.g., determined for a population or particular subpopulation (e.g., selected for race, gender, age, etc.)) using a standard assay protocol. Data derived from processing, analyzing or assaying a test sample is then compared to data obtained for the sample population.

Data obtained from a sufficiently large number of reference samples so as to be representative of a population (or subpopulation) allows the generation of a data set for determining the average level of a particular parameter. Accordingly, the amount of an anti-MAA antibody diagnostic or prognostic of plaque presence, formation of stable plaque, formation of unstable plaque, etc. can be determined for any population of individuals, and for any sample derived from said individual, for subsequent comparison to levels of the expression product determined for a sample being assayed.

It will be recognized that positive or negative results in the assays described herein are not dispositive of a particular presence or absence of a pathological state (e.g., unstable plaque), but rather are typically used in the context of other diagnostic criteria to assist in the in the diagnosis or prognosis of increased risk of development or progression of ischemic cardiovascular disease. Such other diagnostic criteria include, for example, but are not limited to subject medical history, family risk of disease, lifestyle, weight/obesity/BMI, results of other assays such as blood pressure, HDL/LDL ratio, total cholesterol, triglyceride levels, lipoprotein associated phospholipase $A_2$ (LpPLA$_2$), homocystein, C-reactive protein (CRP), HSP70, high density lipoprotein (HDL), TNFα, HSP60, stress tests, imaging studies, and the like. A clinician may also take other factors into account in arriving at a diagnosis or prognosis. In certain embodiments a positive result in the assays described herein can direct the prescribing physician to order other tests or procedures.

Where the individual is considered to have an increased risk of developing ischemic cardiovascular disease (e.g., a myocardial infarction), prophylactic treatments and/or life-style changes may be recommended. Where the individual is diagnosed as having a progressive ischemic cardiovascular disease, his or her clinician may recommend treatments and/or life-style changes tailored to the individual.

Detection/Quantitatation of Anti-MAA Adduct Antibodies in a Biological Sample.

As described above, the level of anti-MAA antibodies in a subject (e.g., a human or a non-human mammal) provides an indicator of the amount/severity and/or of plaque formation in the subject and/or the prognosis for such plaque. Levels of various types of antibodies provide indicators of the risk of an adverse cardiac event (e.g., myocardial infarction, myocardial ischemia, etc.). Thus for example, high anti-MAA adduct IgG and low anti-MAA adduct IgA is an indicator of subjects expected to have an acute myocardial infarction or a heart attack while high anti-MAA adduct IgA, low IgG is an indicator of subjects in whom that plaque formation is more likely to progress in a stable fashion without a heart attack.

Assay methods to detect anti-MAA adduct antibodies in a sample from a subject can be carried out in any of a wide variety of formats. In certain embodiments the subject's levels of antibodies, e.g., IgM, IgG, or IgA antibodies, with reactivity to the MAA adduct can be assessed using immunoassays. Immunoassay formats are preferred, e.g., selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), biosensor technology, evanescent fiber-optics technology, protein chip technology, and the like are also useful. Preferably, the assay is a semi-quantitative assay or quantitative assay.

Examples of suitable immunoassays are described below and will, in view of the teachings provided herein, be apparent to those skilled in the art. For a general review of immunoassays, see Methods in Cell Biology Volume 37: Antibodies in Cell Biology, Asai, ed. Academic Press, Inc. New York (1993); Basic and Clinical Immunology 7th Edition, Stites & Terr, eds. (1991), which is incorporated by reference in its entirety.

In various embodiments the assays can involve assaying for all antibodies with reactivity to MAA protein conjugates, or only for antibodies of a particular isotype, such as IgM, IgG or IgA, or for a combination of two or more antibody isotypes. In certain embodiments at least the level of IgG and/or IgM is determined.

Immunoassays can be competitive or noncompetitive. In a typical competitive immunoassay, the antibody in the sample competes with labeled antibody to bind with the MAA protein adduct. The amount of labeled antibody bound to the MAA protein conjugate is then measured. There is an inverse relationship between concentrations of endogenous anti-MAA adduct antibody in the sample and the quantity of labeled antibody detected.

In noncompetitive immunoassays, antibody in the sample is bound to the PAF conjugate, then a labeled detection reagent, typically an anti-immunoglobulin antibody, is bound to the antibody. The amount of labeled detection reagent bound to the antibody is then measured. Unlike the competitive method, the results of the noncompetitive method will be directly proportional to the concentration of the antibody.

In a noncompetitive immunoassay or western blot, a labeled detection reagent, typically an anti-immunoglobulin antibody, is used to detect antibody (e.g., anti-MAA adduct antibody) bound to the MAA protein adduct. A suitable anti-immunoglobulin antibody is chosen that binds specifically to immunoglobulin of the species from which the sample is obtained. In certain embodiments it may bind to all immunoglobulin isotypes of that species, or only a subset of isotypes. For example, it may bind only to IgA, IgD, IgE, IgG or IgM, or combinations of two or more of these isotypes. In certain embodiments the anti-immunoglobulin antibody may bind specifically only to certain subtypes of any given isotype. Subtypes of human IgA include IgA1 and IgA2. In certain embodiments the anti-immunoglobulin antibody may bind to one or both of these subtypes. Subtypes of human IgG include IgG1, IgG2, IgG3 and IgG4. In certain embodiments the anti-immunoglobulin may bind to one or more of these human IgG subtypes. It will be appreciated that there are different isotypes and subtypes in different vertebrate species.

In radioimmunoassay, the antibody or detection reagent is labeled with a radioisotope, such as $^{131}$I or $^{125}$I. In enzyme immunoassays, the antibody or detection reagent is labeled with an enzyme. In certain embodiments suitable enzymes are capable of being detected with the use of a chromogenic substrate. A chromogenic substrate is a substance which, as a result of the reaction with the enzyme, gives rise to a colored product which can thus be detected spectrophotometrically. Enzymes such as horse radish peroxidase, alkaline phosphatase, beta-galactosidase, and pyrophosphatase from *E. coli* have been widely employed. Chemi-luminescent systems based on enzymes such as luciferase can also be used. Other labels include fluorescent labels such as fluorophores of the Alexa series, quantum dots, electron spin labels, magnetic labels, and the like. In certain embodiments conjugation of the antibody or detection reagent with the biotin is frequently used since this can readily be detected by its reaction with enzyme- or fluorophore-linked avidin or streptavidin to which it binds with great specificity and affinity. Alternatively, in certain embodiments, the antibody/detection reagent is conjugated with streptavidin or avidin that binds a detection reagent linked biotin.

In one illustrative and typical noncompetitive enzyme immunoassay, the sample to be analyzed (e.g., serum) is placed in contact and incubated with a MAA protein adduct (e.g., a MAA/albumin adduct) adsorbed on (or chemically linked to) a solid (or substantially solid) substrate. Any anti-MAA adduct antibodies that are possibly present in the sample are thus specifically bound by the MAA adduct attached to the solid substrate, producing a MAA adduct/anti-MAA adduct antibody complex. The sample is then separated from the solid substrate so as to eliminate non-bound materials, for example, by washing. An indicator antibody capable of binding anti-MAA adduct antibodies that are present on the substrate in the form of a MAA adduct/anti-MAA adduct antibody complex is added to the solid substrate, thus producing a MAA adduct/anti-MAA adduct antibody/indicator antibody complex. The indicator antibody may, for example, be an anti-human IgG immunoglobulin (or anti-human IgM immunoglobulin, or anti-human IgA immunoglobulin, etc.) raised in a non-human animal species. Finally, the presence of the MAA adduct/anti-MAA adduct antibody/indicator antibody complex on the solid substrate is detected and/or quantified, the presence of said complex on the solid substrate being indicative of the presence of anti-MAA protein adduct antibodies in the sample and the amount of the complex being indicative of the amount of anti-MAA protein adduct antibodies in the sample.

In certain embodiments it is preferred that a quantitative estimate of antibody that can bind to the MAA adduct is obtained. In typical non-competitive assays, a linear relationship between the measured variable, whether it be optical density or some other read-out, and antibody concentration, is assumed. For example, if sample A has double the optical density of sample B in the assay (background having been subtracted from both), it is assumed that the concentration of antibody is double in A compared to B. However, it is preferable to construct a standard curve of serial dilutions of a pool of positive samples (e.g., serum samples). In certain embodiments such dilutions are assayed at the same time as the test samples. By doing this, any variation from the linear relationship may be taken into account in determining the quantity of antibody in the samples.

In certain embodiments the solid substrate is a micro-titration plate, for example, of the type commonly used for performing ELISA immunological assays. In certain embodiments the micro-titration plate is preferably a polystyrene plate. Useful solid supports also include, but are not limited to natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxies; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like.

Illustrative solid phase materials well suited for flow-through assay devices include, but are not limited to filter paper such as a porous fiberglass material or other fiber matrix materials. The thickness of such material is not critical and will be a matter of choice, largely based upon the properties of the sample or analyte being assayed, such as the fluidity of the biological sample.

In certain embodiments the solid phase can constitute microparticles (or nanoparticles). Suitable microparticles useful in the methods described herein can be selected by one skilled in the art from any suitable type of particulate material and include, but are not limited to those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of soluble reagents and biological sample or can be retained and immobilized by a support material. In the latter case, the microparticles on or in the support material are typically or preferably not capable of substantial movement to positions elsewhere within the support material. Alternatively, the microparticles can be separated from suspension in the mixture of soluble reagents and biological sample by sedimentation or centrifugation. When the microparticles are magnetic or paramagnetic the microparticles can be separated from suspension in the mixture of soluble reagents and biological sample by a magnetic field.

The methods of the present invention can be adapted for use in systems that utilize microparticle technology including automated and semi-automated systems wherein the solid phase comprises a microparticle. Such systems include those described in pending U.S. Pat. No. 425,651 and U.S. Pat. No. 5,089,424, which correspond to published EPO App. Nos. EP 0 425 633 and EP 0 424 634, respectively, and U.S. Pat. No. 5,006,309.

Thus, for example, it will be appreciated that the illustrative assay described above, can also be performed in a fluid phase. The MAA protein adduct can be provided attached to microparticles or nanoparticles that are contacted with the sample in a suspension. Anti-MAA adduct antibodies present in the sample bind to the MAA protein adduct on the microparticles forming a MAA adduct/anti-MAA adduct antibody complex on the surface of the microparticles. This complex is then contacted with an indicator antibody capable of binding anti-MAA adduct antibodies that are present in the MAA adduct/anti-MAA adduct antibody complex thus producing a MAA adduct/anti-MAA adduct antibody/indicator antibody complex attached to the microparticles. The microparticles can then be separated and the label detected/quantified using for example a cell sorter, or a magnetic separation system.

In certain embodiments, the solid substrate can comprise one or more electrodes. The MAA protein adduct (capture agent) can be affixed, directly or indirectly, to the electrode(s). In one embodiment, for example, the MAA protein adduct can be affixed to magnetic or paramagnetic microparticles, which are then positioned in the vicinity of the electrode surface using a magnet. Systems in which one or more electrodes serve as the solid phase are useful where detection is based on electrochemical interactions. Illustrative systems of this type are described, for example, in U.S. Pat. No. 6,887,714. The basic method is described further below with respect to electrochemical detection.

As indicated above, in various embodiments, the MAA-protein adduct can be attached to the solid support (e.g. ELSA well, microparticle, test strip, etc.) by any of a number of methods. The attachment can be simple adsorption, ionic bonding, or covalent coupling (directly or through a linker). In one illustrative embodiment, the MAA adduct is adsorbed to the solid substrate by incubating the MAA adduct in a buffer with the solid substrate. Suitable buffers include, but are not limited to carbonate buffer or phosphate buffered saline. Typically, after adsorption or covalent linkage of the MAA adduct to the solid substrate, the solid substrate is incubated with a blocking agent to reduce non-specific binding of matter from the sample to the solid substrate. Suitable blocking agents include, but are not limited to bovine serum albumin.

In certain embodiments the intrinsic charge of the solid substrate is altered to facilitate attachment of the MAA adduct, and/or to improve antibody binding, and/or to improve wettability, and the like. In certain embodiments to change or enhance the intrinsic charge of the solid substrate, a charged substance can be coated directly onto the substrate. For example, ion capture procedures for immobilizing an immobilizable reaction complex with a negatively charged polymer, described in EP Patent Publication No. 0326100, and in EP Publication No. 0406473, can be employed to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in EPO Publication No. 0 273, 115.

If the solid substrate is silicon or glass, the surface is often activated prior to attaching the capture agent (e.g., the MAA protein adduct). Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl] aminobenzoate), and SMPB (succinimidyl 4-[1maleimidophenyl] butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a MAA protein adduct on a solid phase using techniques and chemistries described U.S. Pat. Nos. 5,459,080, 5,459,078, and the like.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

MAA Protein Adduct

In various embodiments a MAA protein adduct is used to capture/bind anti-MAA adduct antibodies that are present in the biological sample. Methods of making a MAA protein adduct are known to those of skill in the art and described, for example, in U.S. Pat. No. 5,939,535 and in Tuma et al. (1996) *Hepatology*, 23(4): 872-880. Basically acetaldehyde and malondialdehyde (MDA) react together in the presence of a protein (a substrate with an amino group) to form a distinct product comprising a hybrid adduct of MDA and acetaldehyde which has been designated malondialdehyde, acetaldehyde-adduct (MAA).

As described in U.S. Pat. No. 5,939,535, the adduct can readily be produced by treatment of the protein(s) of interest (e.g., albumin), e.g., at a concentration of 1 mg/ml with 1 mM acetaldehyde plus 1 mM MDA for 3 days at 37° C. Following overnight dialysis against 0.1 M phosphate buffer (pH 7.4 and 4° C.), the solution can be further handled as desired (e.g., adsorbed or covalently coupled to an ELISA well, microparticle, etc.).

However, depending on the type of macromolecule, concentrations of AA and MDA may need to be raised or lowered to achieve the same amount of fluorescents that makes MAA reactive.

The method of producing a MAA protein adduct is illustrative and non-limiting. Using the teachings provided herein, the MAA adducts can readily be produced using other methods.

Labeling Systems

Detectable labels suitable for use in the detection agents (e.g., antibodies that bind to anti-MAA adduct antibodies and form an anti-MAA adduct/anti-MAA adduct antibody complex) in the assays described herein include any composition detectable by spectroscopic, photochemical, biochemical, immunochemical, electrical, optical, or chemical means. Useful labels include, but are not limited to, magnetic beads (e.g., DYNABEADS®), fluorescent dyes (e.g., fluorescein, Texas Red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^{3}H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and U.S. Pat. No. 4,366,241.

The label can be attached to the detection agent prior to, or during, or after contact with the biological sample. So-called "direct labels" are detectable labels that are directly attached to or incorporated into detection agents (e.g., anti-IgG antibodies, anti-IgM antibodies, anti-IgA antibodies, etc.) prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542). Such polypeptides can thus be labeled and added to the assay mixture, where they will bind to the detection antibody, as well as to the species-specific antibody, labeling both and providing a composite signal attributable to analyte and autoantibody present in the sample.

Some labels useful in methods described herein require the use of an indicator reagent to produce a detectable signal. In an ELISA, for example, an enzyme label (e.g., beta-galactosidase) may require the addition of a substrate (e.g., X-gal) to produce a detectable signal.

Illustrative Formats

Chemiluminescent Microparticle Immunoassay (CMIA)

In one illustrative embodiment a chemiluminescent label is employed in a chemiluminescent microparticle assay (CMIA) according to the invention. Generally, chemiluminescent microparticle assay techniques are based on the principle that a chemiluminescent label, when treated via a trigger reagent, will emit light at a characteristic wavelength (i.e., chemiluminescence).

The reactants necessary for CMIA can include microparticles coated with a capture agent specific for the analyte being measured, a chemiluminescent detection agent and a triggering agent (e.g., chemical or electrochemical). The reaction sequence for performing CMIA can include mixing the microparticles coated with a capture agent specific for the analyte with a sample in a reaction vessel to form an immune complex; washing the captured immune complex to remove unbound material; mixing the captured immune complex with a chemiluminescent detection agent; washing the captured immune complex-chemiluminescent detection agent; and mixing the captured immune complex-chemiluminescent detection agent with a triggering agent to initiate light emission.

Chemiluminophores useful in CMIA include acridinium (e.g. acridinium-9-carboxamide), luminol, dioxetane, ruthenium complexes and similar chemiluminescent derivatives. Microparticles useful in CMIA include diamagnetic, magnetic and paramagnetic microparticles. Examples of commercially available automated instruments with which chemiluminescent microparticle assay assays can be conducted include: Architect i-Systems and the Abbott Prism (all available from Abbott Laboratories, Abbott Park, Ill.).

Electrochemical Detection Systems

In other embodiments, immunoassays are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 μL to 360 μL have been reported previously. In capillary immunoassays with electrochemical detection, the lowest detection limit reported thus far is 3000 molecules of mouse IgG using a volume of 70 μL and a 30 min or 25 min assay time.

In one illustrative approach a test cartridge (similar to the Abbott Point of Care (i-STAT™) electrochemical immunoassay system) provides a MAA protein adduct on an electrochemical sensor fabricated in a silicon chip. Deposited in another location on the chip is an antibody/alkaline phosphatase conjugate (e.g., an anti-IgG conjugated to alkaline phosphatase). The biological sample (e.g., whole blood, plama, etc.) is contacted with the sensor allowing the enzyme conjugate to dissolve into the sample. Anti-MAA adduct antibodies within the sample become labeled with the conjugate and this complex is captured onto the surface of the electrochemical sensor by binding of the anti-MAA adduct antibodies to the immobilized MAA adduct. The sample, as well as excess enzyme conjugate, is washed off the sensors. Within the wash fluid is a substrate for the alkaline phosphatase enzyme. The enzyme bound to the antibody/antigen/antibody sandwich cleaves the substrate releasing an electrochemically detectable product. The electrochemical (e.g., amperometric, voltammetric, etc.) sensor measures this enzyme product which is proportional to the concentration of anti-MAA adduct antibodies in the sample.

This electrochemical detection scheme is intended to be illustrative and not limiting. It is noted that other electrochemical detection methods are known to those of skill in the art and various electrochemical detection systems are described, for example, in U.S. Pat. Nos. 7,045,364, 7,045,310, 6,887,714, 6,682,648, 6,670,115, and the like.

Lateral Flow Assays.

In certain embodiments the assays are formatted as lateral flow tests also known as lateral flow immunochromatographic assays. These assays are often produced in a test strip/dipstick format. In lateral flow assays the test sample flows along a solid substrate via capillary action. After the sample is applied to the test it encounters a colored reagent that mixes with the sample and transits the substrate encountering lines or zones that have been pretreated with (e.g., with antigen such as MAA adduct) and/or detection reagent (e.g., labeled antibody). Depending upon the analytes present in the sample the colored reagent can become bound at the test line or zone and can be quantified by comparison to a reference, or read electrochemically as described herein, or read optically using for example a reader. Lateral Flow Tests can operate as either competitive or sandwich assays.

Microfluidic Assays.

In certain embodiments the assays are performed using microfluidic devices. Microfluidic assays are well known to those of skill in the art. In one illustrative approach, fluorescent reactions of a heterogeneous sandwich enzyme-linked immunoassay (ELISA) in an all-PDMS [poly (dimethylsiloxane)] microfluidic device can be detected using a cooled charge coupled device (CCD) camera interfaced with an epifluorescence microscope. A PDMS chip microsensor has been successfully used to quantify a model analyte (sheep IgM) with sensitivity down to 17 nM. This hybrid integrated technique has been extended to on-chip imaging and quantification of light emission from a biochemical immunoassay in PDMS chip (see, e.g., Eteshola and Balberg (2004) *Biomedical Microdevices*, 6(1): 7-9, and the like).

Multiplex Formats

In particular embodiments, useful, for example, for simultaneously assaying multiple analytes in one biological sample (e.g. anti-MAA IgG, IgM, and IgA), the assay system can include a plurality of different detection agents (e.g., anti-IgG, anti-IgM, anti-IgA, etc.) and, in certain embodiments, these different detection agents can be localized at different reaction sites (e.g., different wells in an ELISA plate). Thus, the assays can be multiplexed. During a single assay run, the solid phase can have a plurality of different regions on a surface, wherein each region has affixed antibodies of a particular specificity.

This can also be accomplished in a solution phase where detection reagents specific for each antibody serotype are labeled with different labels. After reaction these can be separated and/or quantified using, e.g., a cell sorter.

Multiplex formats can, but need not, employ a plurality of labels, wherein each label is used for the detection of a particular analyte and/or auto-antibodies specific for that analyte. For example, multiple analytes can be detected without using a plurality of labels where different detection agents are used at different locations on the support (e.g., in different wells of an ELISA plate). Because the specificity of the detection agent at each location is known, the detection of a signal at a particular location can be associated with the presence of specific anti-MAA adduct antibodies bound at that location. Examples of this format include microfluidic devices containing different labeling agents at different locations along a channel. In certain embodiments, a different label reagent can be associated with a different electrode system where multiple electrode systems (e.g., an IgG detection system, and IgA detection system, and an IgM detection system) can be fabricated in a single microchip/microfluidic device.

In addition to the various immunoassays described above (e.g., direct ELISA, indirect ELIAS), etc. other assay formats will be available to detect anti-MAA adduct antibodies. Such assays include, but are not limited to RIP assays, BIAcore assays, evanescent field assays, and the like.

RIP assays measure antibody binding to cognate antigens in a fluid phase. Thus, anti-MAA adduct antibodies can be detected and quantified with radiolabeled MAA protein adducts and precipitating agents, such as protein A-Sepharose or protein G-Sepharose, which bind to the Fc portion of antibodies and are used to collect antigen-antibody complexes by centrifugation (Bendtzen et al. (2000) *Mol. Biotechnol.* 14: 251-261). An illustrated example of a typical RIP testing platform is described by Prabhakar and Muhlfelder (1997) *Clin. Nephrol.* 47: 331-335, and was used to detect human antibodies against recombinant EPO.

BIAcore immunoassays use surface plasmon resonance to optically measure antibodies that bind to target antigens (e.g., MAA protein adduct) immobilized on a special dextran-coated glass surface. The signal in the BIAcore assay directly increases as the mass of antibody accumulates on the surface of the sensor chip. The BIAcore immunoassay to characterize/quantify antibodies is well known to those of skill in the art (see, e.g., Meager et al. (2003) *Clin. Exp. Immunol.* 132: 128-136; VanCott et al. (1992) *J. Immunol. Meth.,* 146: 163-176; Takacs et al. (1999) *J. Interferon Cytokine Res.* 19:781-789; Swanson (2003) Pp. 127-133. In A. R. Mire-Sluis (ed.) *Immunogenicity of therapeutic biological products*, vol. 112. Karger, Basel, Switzerland; Swanson (2004) *Nephron. Clin Pract.* 96:c88-c95; and the like).

In certain embodiments evanescent biosensors are also contemplated. These biosensors do not require the pretreatment of a biological sample prior to detection of an analyte of interest. An evanescent biosensor generally relies upon light of a predetermined wavelength interacting with a fluorescent molecule, such as for example, a fluorescent label attached to a MAA adduct near the probe's surface, to emit fluorescence at a different wavelength upon binding of the analyte (e.g. anti-MAA adduct antibody).

It will be apparent to the skilled person that the assay formats described herein are amenable to any of a number of high throughput formats.

Biological Samples

In various embodiments the anti-MAA adduct antibody measurements are made on biological samples derived from a subject of interest. Such subjects include, for example, a patient displaying one or more clinical symptoms, an asymptomatic patient undergoing routine examination, a patient displaying one or more cardiac risk factors (e.g., obesity, diabetes, smoker, family history of heart disease, etc.).

The sample is obtained using standard methods known to those of skill in the art, and in certain embodiments, ultimately standardized for a particular assay protocol. Typically the biological sample will be one in which anti-MAA adduct antibodies are expected to be found if they are present at all in the subject. Such samples include, but are not limited to saliva/sputum, blood or blood fractions (e.g., plasma, serum), certain tissue biopsies, and the like.

In one embodiment a biological sample is obtained from a subject by a method selected from the group consisting of surgery or other excision method, aspiration of a body fluid such as hypertonic saline or propylene glycol, broncheoalveolar lavage, bronchoscopy, saliva collection with a glass tube, salivette (Sarstedt AG, Sevelen, Switzerland), Ora-sure (Epitope Technologies Pty Ltd, Melbourne, Victoria, Australia), omni-sal (Saliva Diagnostic Systems, Brooklyn, N.Y., USA) and blood collection using any method known in the art, such as, for example using a syringe.

In various embodiments the sample may be treated to facilitate storage and/or processing in the assay, and/or standardization of the assay.

Imaging Plaque In Vivo

Imaging Compositions and their Use

In certain embodiments, methods are provided for imaging plaques, in particular unstable plaques that can result in a myocardial infarction. In various embodiments the methods entail administering to the subject of interest a composition that specifically or preferentially binds a MAA protein adduct where the composition comprises a detectable label. Thus, the targeting composition typically comprises a targeting moiety (e.g., an anti-MAA adduct antibody attached to a detectable label). When administered to a subject, the targeting moiety specifically or preferentially binds to sites where the MAA protein adduct is presented. This results in localization/preferential distribution of the label to such sites. Where the composition is administered to the subject's vasculature, the label will localize or preferentially distribute to sites of plaque formation with more label being localized at plaques that are further developed and/or unstable. The subject is imaged and the location of the label detected. This permits evaluation of the plaque and provides a guide for subsequent action (e.g., medication, angioplasty, bypass surgery, etc.).

The labeling composition can be used in a direct targeting approach or in a pretargeting strategy. In direct targeting, the detectable label is attached to a targeting moiety that specifically or preferentially binds a MAA adduct (e.g. anti-MAA antibody, antibody fragment, etc.). Binding of the antibody to the anti-MAA adduct in the region of plaque formation thus localizes the label in that region which can then be imaged providing an indication of the location, and/or severity of the plaque.

In certain embodiments the labeling composition can be used in a "pretargeting" strategy). In this approach the label is not initially attached to the MAA adduct targeting moiety. Rather the MAA adduct targeting moiety (e.g., anti-MAA adduct antibody) is attached to a second moiety that can later be bound by an agent bearing the detectable label. Suitable second moieties include, for example, epitope tags, antibody constant region or framework regions, biotin avidin, and the like.

In certain embodiments, the label utilized in such labeling compositions is a "radio-opaque" label, e.g., a label that can be easily visualized using x-rays. Radio-opaque materials are well known to those of skill in the art. The most common radiopaque materials include iodide, bromide or barium salts. Other radio-opaque materials are also known and include, but are not limited to organic bismuth derivatives (see, e.g., U.S. Pat. No. 5,939,045), radiopaque polyurethanes (see U.S. Pat. No. 5,346,981, organobismuth composites (see, e.g., U.S. Pat. No. 5,256,334), radiopaque barium polymer complexes (see, e.g., U.S. Pat. No. 4,866, 132), and the like.

In addition to radio-labels, other detectable labels are also suitable for use such labeling compositions. Such labels include for example radioactive labels and/or labels detected by MRI, NMR, PET, and the like.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. Particular useful PET labels include, but are not limited to $^{11}$C, $^{18}$F, $^{15}$O, $^{13}$N, and the like. Common labels used in MRI include, but are not limited to gadolinium chelates and iron oxide nanoparticles or microparticles with various surface modifications. Gadolinium chelates, such as gadopentate dimeglumine, are the most widely used paramagnetic contrast material. Iron oxide particles are part of a class of superparamagnetic MRI contrast agents. These compounds typically consist of magnetite (iron oxide) cores are coated with dextran or siloxanes, encapsulated by a polymer, or further modified.

The targeting moiety (e.g., anti-MAA adduct antibody, etc.) can be attached directly to the detectable label or it can be attached by means of one or more linkers. For example, the targeting moiety and the detectable label moiety can be conjugated via a single multifunctional (e.g., bi-, tri-, or tetra-) linking agent or a pair of complementary linking agents. In another embodiment, the targeting moiety and the label are conjugated via two, three, or more linking agents.

A "linker" or "linking agent" as used herein, is a molecule that is used to join two or more molecules. In certain embodiments the linker is typically capable of forming covalent bonds to both molecule(s) (e.g., the targeting moiety and the effector). Suitable linkers are well known to those of skill in the art and include, but are not limited to, straight or branched-chain carbon linkers, heterocyclic carbon linkers, or peptide linkers.

A bifunctional linker having one functional group reactive with a group on one molecule (e.g., an anti-MAA antibody), and another group reactive on the other molecule (e.g., the detectable label), can be used to form the desired conjugate. Alternatively, derivatization can be performed to provide functional groups. Thus, for example, procedures for the generation of free sulfhydryl groups on peptides are also known (see, e.g., U.S. Pat. No. 4,659,839).

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccinimidyl chloroformate, enzymatic oxidation, alkyl halogens, and isocyanates. Aldehyde and ketone reactive groups include, but are not limited to e.g., hydrazine derivatives for Schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 198, American Chemical Society, Washington, D.C.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075).

Many of the imaging reagents described herein can be provided as a chelate, particularly where a pre-targeting strategy is utilized. The chelating molecule is typically coupled to a molecule (e.g., biotin, avidin, streptavidin, etc.) that specifically binds an epitope tag attached to a prostate cancer specific antibody of this invention.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'—,N''',N''''-tetra-acetic acid (DOTA), hydroxyethyldiamine triacetic acid (HEDTA), 1,4,8,11-tetra-azacyclotetradecane-N,N',N''',N''''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N'', N''''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl): 154P, which discloses the linkage of DOTA to biotin via available amino side chain biotin derivatives such as DOTA-LC-biotin or DOTA-benzyl-4-(6-amino-caproamide)-biotin). PCT Publication WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$In and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

It is noted that the macrocyclic chelating agent 1,4,7,10-tetraazacyclododecane-N,N',N'',N'''-tetraacetic acid (DOTA) binds $^{90}$Y and $^{111}$In with extraordinary stability. Kinetic studies in selected buffers to estimate radiolabeling reaction times under prospective radiopharmacy labeling can be performed to determine optimal radiolabeling conditions to provide high product yields consistent with FDA requirements for a radiopharmaceutical. It is also noted that protocols for producing Yttrium-90-DOTA chelates are described in detail by Kukis et al. (1998) *J. Nucl. Med.*, 39(12): 2105-2110.

Methods of producing chelates suitable for coupling to various targeting moieties (e.g., anti-MAA adduct antibodies) are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, 6,001,329, and the like).

Means of detecting such labels are well known to those of skill in the art. Thus, for example, radiolabels may be detected using photographic film, scintillation detectors, and the like. PET labels are detected/visualized using PET imaging systems. Similarly MRI labels are detected/visualized using MRI systems.

Antibody Production.

In certain embodiments the labeling reagent for in vivo detection of MAA adducts comprises an anti-MAA antibody. Antibodies useful in such compositions include polyclonal and monoclonal antibodies, antibody fragments, single chain antibodies and the like. Polyclonal antibodies are raised by injecting (e.g., subcutaneous or intramuscular injection) an immunogen (e.g., a MAA adduct) into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) *Nature*, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552-554; Hoogenboom et al. (1991) *Nucleic Acids Res.* 19: 4133-4137).

Since the antibody fragments on the surface of the phage are functional, phage-bearing antigen-binding antibody fragments can be separated from non-binding phage by antigen affinity chromatography (McCafferty et al. (1990) *Nature*, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. *Mol. Biol.* 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) *J. Mol. Biol.* 222: 581-597; Marks et al. (1993). *Bio/Technology.* 10: 779-783; Griffiths et al. (1993) *EMBO J.* 12: 725-734; Clackson et al. (1991) *Nature.* 352: 624-628).

In addition, it is noted that the production of antibodies that specifically bind MAA adducts is described in U.S. Pat. No. 5,939,535. As described therein, a MAA-adduct immunogen was prepared by the treatment of rabbit plasma proteins (prepared by ammonium sulfate precipitation as described by Klassen (1994) *Alcohol Clin Exp Res.* 18:164-171) at a concentration of 1 mg/ml with 1 mM acetaldehyde plus 1 mM MDA for 3 days at 37° C. Following overnight dialysis against 0.1 M phosphate buffer (pH 7.4 and 4° C.), the solution was mixed with an equal volume of Freund's complete adjuvant and emulsified. New Zealand white rabbits were injected subcutaneously in four sites along their backs (400 µg of modified protein). After two and four weeks, the rabbits were boosted by the same procedure except Freund's incomplete adjuvant was used. Two weeks after the final injection, serum was obtained and tested for antibody activity.

The resulting antisera was then affinity purified. Lysine derivatized Sepharose 4B beads (Sigma Chemical Co., St. Louis, Mo.) were modified by adding acetaldehyde (1 mM) and MDA (1 mM) in 0.1 phosphate buffer, pH 7.4, and incubating at 37° C. for 3 days with constant shaking. The beads were washed with four volumes of buffer and poured into a 0.7 cm.times.15 cm low pressure Econo-Column (Bio-Rad Laboratories, Hercules, Calif.). Ten ml of rabbit serum from the immunized animals were loaded onto the column. The column was washed with 5 volumes of buffer, followed by 1 M NaCl, and then eluted with 0.5 M acetic acid (pH 2.5) into Tris buffer (pH 8.2) to neutralize the acid. The eluted material was further purified by Protein G-Sepharose B (Pharmacia, Piscataway, N.J.) column chromatography, yielding a purified IgG fraction of greater than 95%.

As those of skill in the art readily appreciate, antibodies can also be prepared by any of a number of commercial services (e.g., Berkeley Antibody Laboratories, Bethyl Laboratories, Anawa, Eurogenetec, etc.).

Diagnosis/Prognosis of Other Disorders Characterized by an Inflammatory Process.

It was also discovered that the malondialdehyde-acetaldehyde adduct (MAA) can serve as a bio-marker for inflammation in many diseases. This stems from the basic nature of the components involved in the formation of this adduct. Without being bound to a particular theory, it is believed that following tissue damage cellular membranes are recognized by various phagocytic cells (macrophages and neutrophils). During this process, the phagocytes release superoxides that alter the cell membrane lipids to produce malondialdehyde (MDA). When sufficient levels of MDA are produced then the MAA adduct will result. As such, the presence of MAA in tissues is a reflection of the amount of tissue/cellular damage that occurs during inflammatory responses and its detection is a good marker for this inflammation.

The MAA adduct has been shown to have many pro-inflammatory and immune stimulating properties that could result in the development of antibody to both the MAA adduct and macromolecule to which it is attached (See our second patent, other papers). Therefore, the presence of anti-MAA antibodies reflects the amount of MAA formed in the tissues during inflammatory responses. Additionally, the generation of monoclonal and polyclonal antibodies to MAA has made it possible to assess inflammatory responses in various diseases.

Accordingly in certain embodiments it is contemplated that the MAA adduct and/or antibodies to the MAA adduct can be used as a marker of inflammation in a number of pathologies characterized by an inflammatory response.

Examples of conditions characterized by an inflammatory response include, but are not limited to rheumatoid arthritis, atherosclerosis (as indicated above), chronic obstructive pulmonary disease (COPD), emphysema, asthma, infections (e.g., bacterial, viral, parasitic), sepsis/sepsis syndrome, inflammatory bowel disease, lupus, multiple sclerosis, connective tissue diseases, hepatitis, eczema, and the like.

Accordingly in certain embodiments, a method for evaluating a subject for risk, status, stage, progression, or severity of an inflammatory condition, is provided. The method typically comprises determining the level of MAA adduct and/or an anti-MAA adduct in a biological sample derived from the subject where an elevated level of MAA adduct and/or anti-MAA antibody (as compared to a normal healthy subject, and/or as compared to the same subject at an earlier time) indicates increased risk, status, stage, progression, and/or severity of the inflammatory condition. In certain embodiments the sample comprises a sample is selected from the group consisting of a urine sample, a serum sample, a plasma sample, blood, a blood fraction, oral fluid/sputum, bronchial lavage, a synovial fluid sample, a fecal sample, a tissue biopsy, and a cerebrospinal fluid sample.

It will be appreciated that the particular condition that the inflammatory states is characteristic of can readily be determined in the context of a differential diagnosis, e.g., by consideration of other risk factors, patient history, lifestyle, and other test results.

Assays for MAA adduct and/or anti-MAA adduct antibodies can be performed according to standard methods well known to those of skill in the art.

Kits

Diagnostic/Prognostic Assay Kits

In certain embodiments kits for detecting and/or quantifying anti-MAA adduct antibodies in a biological sample are contemplated. In one embodiment the kit comprises a container containing a MAA protein adduct that can be provided as a lyophilized dry powder, in solution, or attached to a solid support (e.g., a microtiter plate, microbeads, etc.). The kits can optionally further include one or more reagents for detecting a MAA-adduct/anti-MAA adduct complex. Such reagents can include an anti-MAA antibody (e.g., anti-MAA antibody IgG, and/or IgM, and/or IgM). The kit can further comprise a reporter molecule such as, for example, an enzyme (such as horseradish peroxidase or alkaline phosphatase), a substrate, a cofactor, an inhibitor, a dye, a radionucleide, a luminescent group, a fluorescent group, biotin or a colloidal particle, such as colloidal gold or selenium. Preferably such a reporter molecule is directly linked to the detection reagent antibody.

In certain embodiments the kit additionally comprises a reference sample. Such a reference sample may for example, comprise a standard solution of one or more anti-MAA adduct antibodies.

In yet another embodiment, a kit optionally comprises means for sample preparations, such as, sample collection devices, sample storage vessels, buffers, enzyme substrates, and the like.

In addition, the kits optionally include labeling and/or instructional materials providing directions (e.g., protocols) for the practice of the diagnostic/prognostic methods described herein. Preferred instructional materials describe the detection of anti-MAA adduct antibodies (e.g., IgG, and/or IgM, and/or IGA) to diagnose the presence of plaques and/or to evaluate the prognosis for plaque formation (e.g., formation of stable or unstable plaques).

Imaging Kits.

In certain embodiments kits for detecting and/or quantifying MAA adduct in vivo (e.g., for imaging plaque in vivo) are provided. In certain embodiments these kits comprise a container containing an anti-MAA adduct antibody. In certain embodiments the kit can further comprise a detectable label (e.g., a radio-opaque label, an MRI label, a PET label, an NMR label, an ESR label, etc.). The kits can optionally further include one or more reagents and/or devices for administering and/or detecting the anti-MAA antibody in vivo.

In addition, the kits optionally include labeling and/or instructional materials providing directions (e.g., protocols) for the use of MAA adduct imaging reagents to detect and/or localize, and/or visualize plaque.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Ox-LDL and Proteins Modified with Aldehydes Induce Pro-Inflammatory, Immune and Atherosclerotic Effects Through the Malondialdehyde/Acetaldehyde (MAA) Adduct Common to Both Ox-LDL and subsequent uptake by macrophages located on the vascular wall of the aorta have long been known to increase the risk of atherosclerotic lesions and the formation of plaques. Malondialdehyde/acetaldehyde modified proteins (MAA) are present and appear to correlate with the development and progression of human atherosclerosis. It was the purpose of this study to determine whether there is a relationship between MAA modified proteins and Ox-LDL that may explain their potential roles in the development of atherosclerosis.

Methods.

The mouse aortic endothelial cell line CRL-2167 was used to determine whether it was possible for MAA-modified proteins or Ox-LDL to induce cytokine expression and/or secretion. Briefly, these cells were exposed to different concentrations of; LDL, Ox-LDL, human serum albumin (HSA) or HSA-MAA, and analyzed for cytokine expression (mRNA) and secretion (protein). To assess whether these responses were due to similarities in the modified ligands, Balb/c mice were immunized with LDL, Ox-LDL, LDL-MAA, HSA, or HSA-MAA and serum tested for the presence of antibodies to MAA and LDL. These ligands were analyzed for MAA using antibodies previously reported to be specific for this epitope. Aortic tissues were extracted from JCR rats and probed by Western blot for MAA-modified proteins.

Results and Conclusions mRNA expression and protein secretion studies demonstrated increases in MCP-1, IL-6, TNF-α, and smooth muscle actin following incubation with HSA-MAA, Ox-LDL and LDL-MAA. Serum from mice immunized with the various ligands showed antibody to MAA was produced only in those mice immunized with Ox-LDL, LDL-MAA and HSA-MAA. Anti-MAA antibodies showed that only these three immunizing ligands contained this adduct. Immunization with LDL-MAA also resulted in the production of potentially pathogenic anti-LDL antibodies. Finally, aortas from JCR rats contained MAA modified proteins as assessed by Western blotting using the anti-MAA antibodies. In conclusion, MAA modified proteins and Ox-LDL result in antibody responses and pro-inflammatory effects which may increase atherosclerotic disease through the MAA moiety common to both.

Example 2

New Biomarkers for the Assessment of Vulnerable Plaque in Patients with Atherosclerosis Disease and Acute Myocardial Infarction Oxidized proteins have been implicated in the development and progression of atherosclerosis. Malondialdehyde (MDA)-acetaldehyde (AA) adduct (MAA), is produced and is the dominant epitope formed following incubation of proteins with the oxidative product MDA. The purpose of this study was to evaluate anti-MAA adduct antibody as a marker for cardiac artery disease.

Serum samples from normal controls, patients with acute myocardial infarction (MI), early coronary artery disease (CAD), and late state coronary artery disease were analyzed for antibodies to the MAA protein adduct (biomarker).

Figure 3:
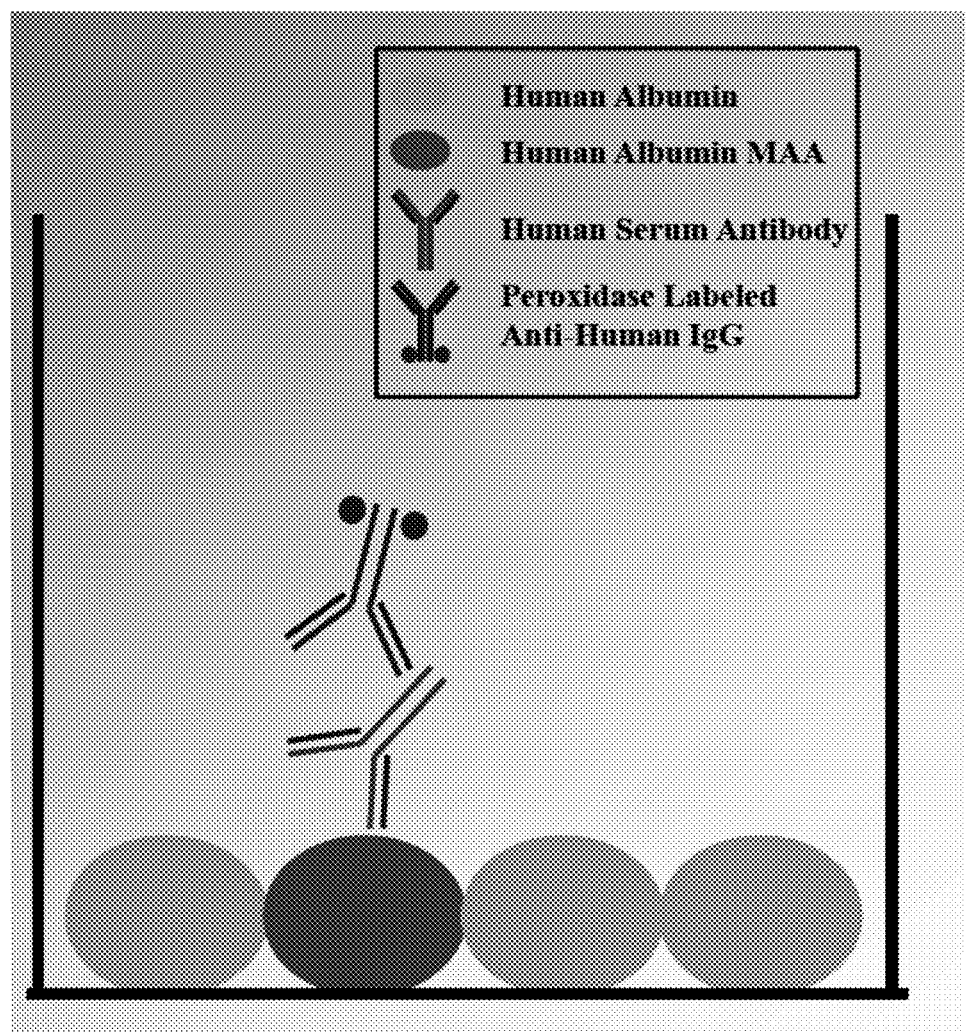
FIG. 3 schematically illustrates one assay format for anti-MAA antibodies.

To determine MAA protein adduct in the serum samples, ELISA plates were coated with human albumin or human albumin MAA. Sera from subjects were diluted and added to the appropriate wells. Antibody binding was detected using a peroxidase-labeled anti-human IgG second antibody (as illustrated in FIG. 3). Optical density was determined and concentrations of anti-MAA adduct antibody extrapolated from a human IgG standard curve. Anti-MAA adduct antibody concentration was determined as concentration of antibody to MAA-albumin minus the antibody concentration to albumin alone.

Figure 4:
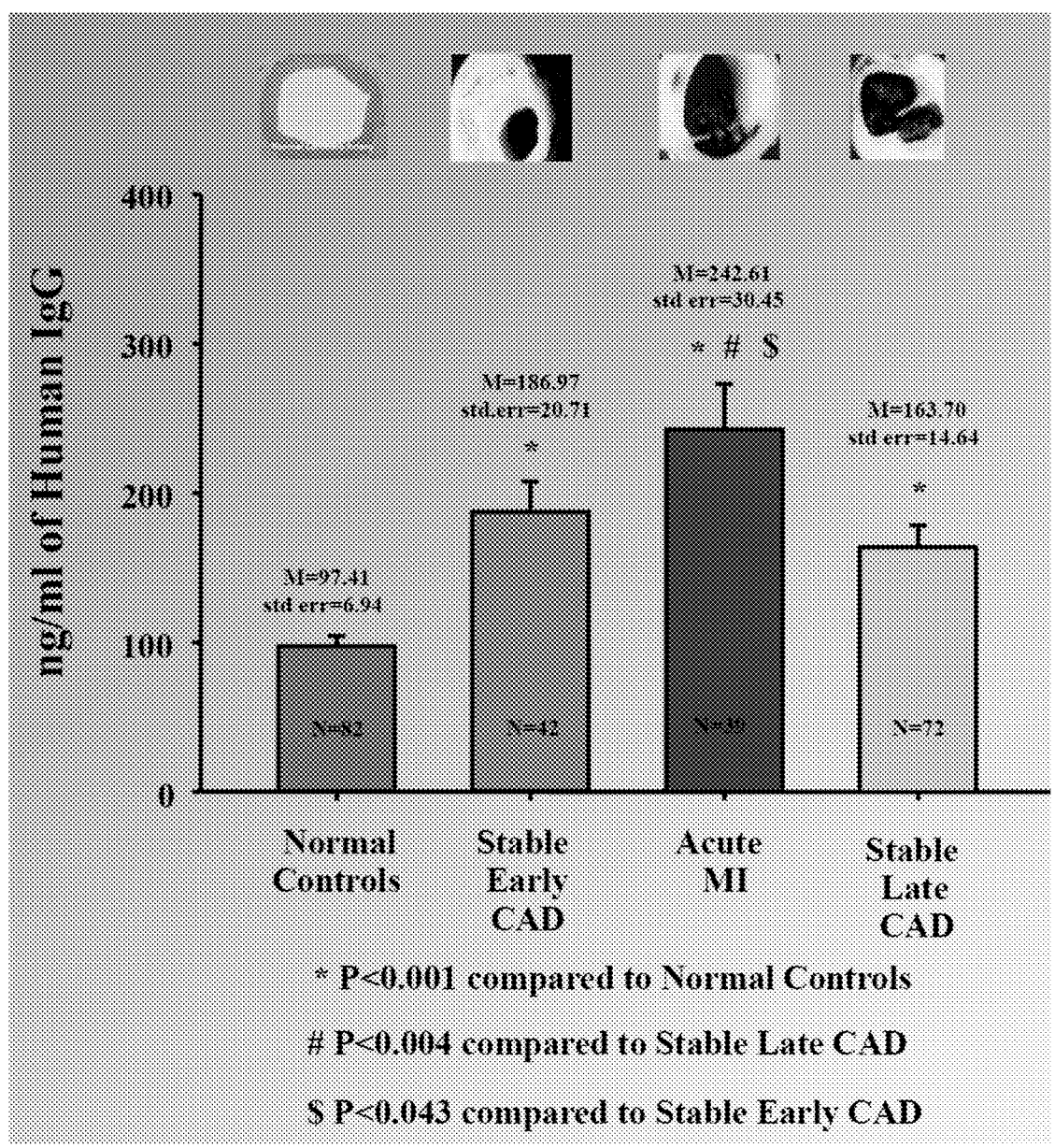
FIG. 4 illustrates Serum Concentration of MAA in normal controls as compared to individuals with known coronary artery disease (CAD).

As illustrated in FIG. 4, subjects with acute MI had significantly higher levels of anti-MAA adduct antibody as compared to normal controls, subjects with early stage CAD and subjects with late stage CAD.

Figure 5:
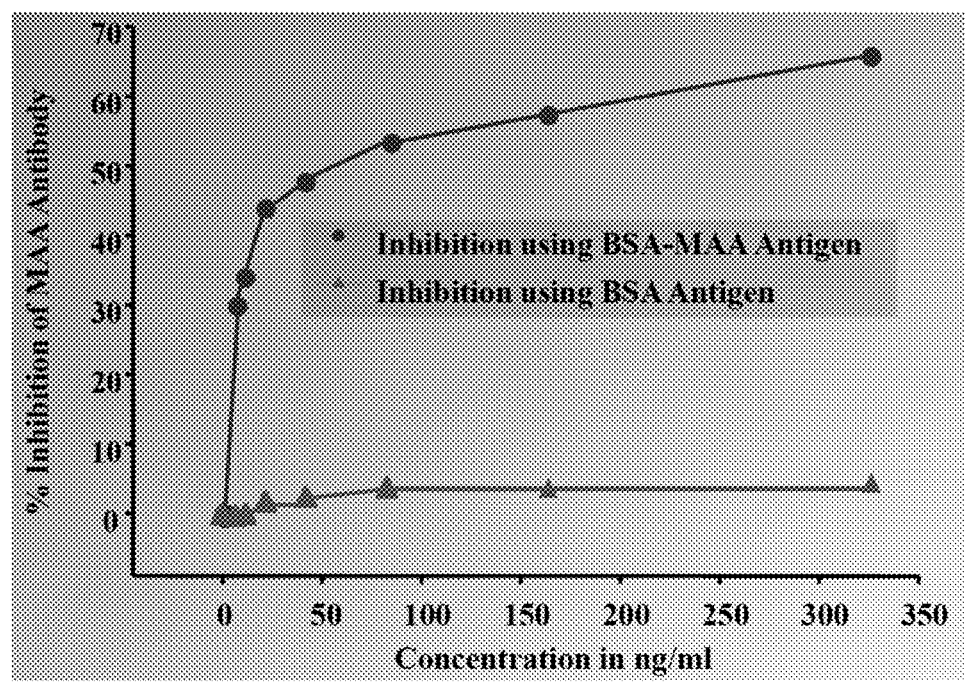
FIG. 5 illustrates the percent inhibition by MAA albumin of circulating MAA antibody in patients with acute MI. This provides a measure of assay specificity.

There were questions as to the specificity of the assay above, so a study was done to show that the antibody detected is the antibody to the adduct MAA. Serum antibody concentrations were inhibited using bovine serum albumin (BSA) and BSA modified with MAA (BSA-MAA). Antibody was held at a constant dilution and different concentrations of BSA or BSA-MAA was used as the inhibitor. The antibody and inhibitor were incubated together and then added to wells of the assay and developed as described above. The resulting data, presented as percent inhibition, are presented in FIG. 5. As shown therein MAA specific antibody comprises approximately 70% of the signal.

Figure 6:
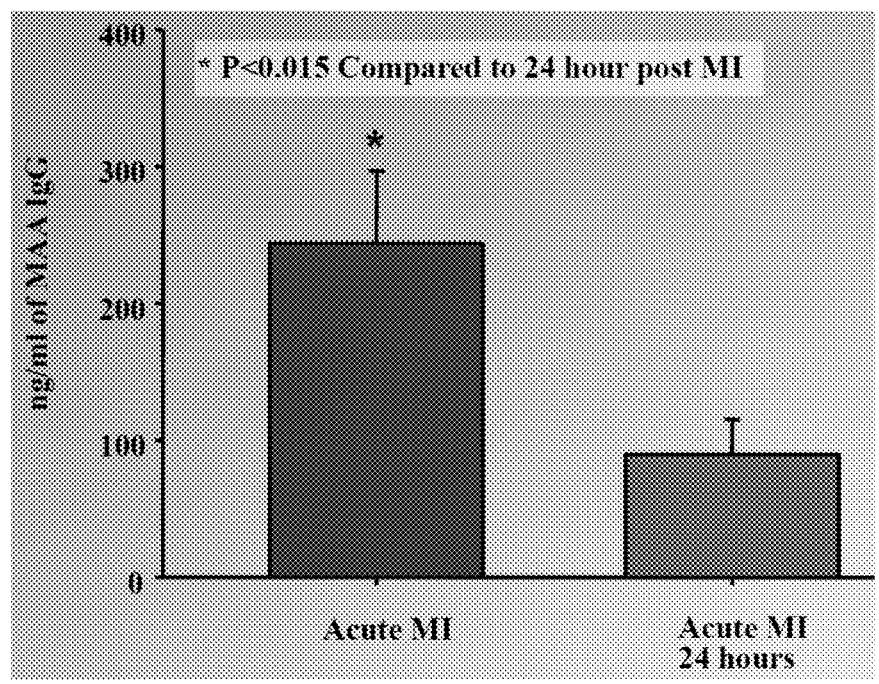
FIG. 6 illustrates serum concentration of antibody to MAA in patients with acute myocardial infarction at the time of the event and 24 hours post event.

An interesting observation was made in the course of these studies with respect to the antibody to MAA. Serum was collected at the time of myocardial infarction (MI), and 24 hours following stabilization. As shown in FIG. 6, antibody concentration was significantly decreased 24 hours after MI. Without being bound to a particular theory, it is believed this is due to binding and sequestering of the antibody by modified proteins that are produced when tissue is damaged and released during the MI.

Figure 7:
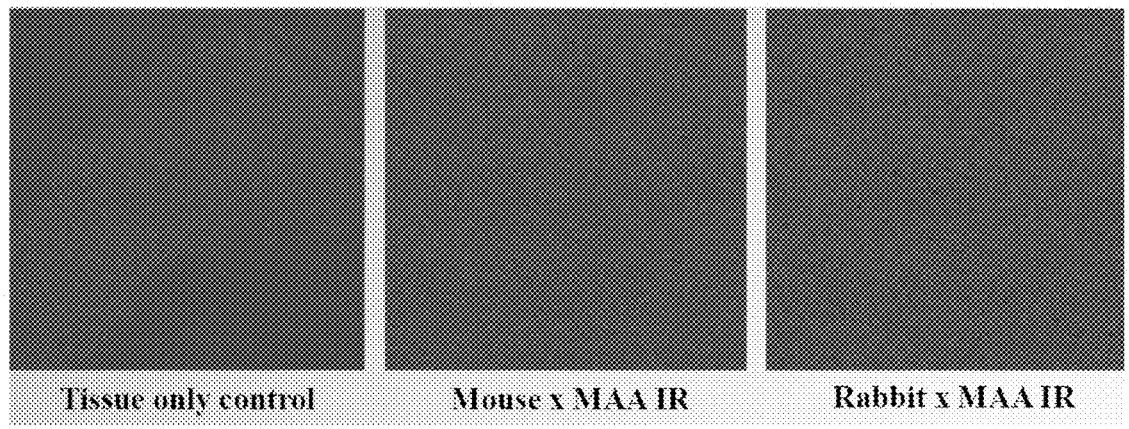
FIG. 7 illustrates the presence of MAA in aortic punch biopsy from coronary artery bypass grafting (CABG) patients.

The presence of MAA in Aortic Punch Biopsy from coronary artery bypass grafting (CABG) patients was also examined. Aortic punch biopsies from coronary artery bypass grafting (CABG) patients stained with antibodies to MAA. The results are shown in FIG. 7. Tissue was blocked with mouse (middle panel) or rabbit serum (right panel) and then incubated with mouse or rabbit anti-MAA that was directly labeled with an infrared particle (680 nm). Slides were evaluated by Confocal Microscopy (63x). Autofluorescence of tissue is represented by the tissue in the left panel. As illustrated in FIG. 7, MAA is present in the aortas of these patients.

Figure 8:
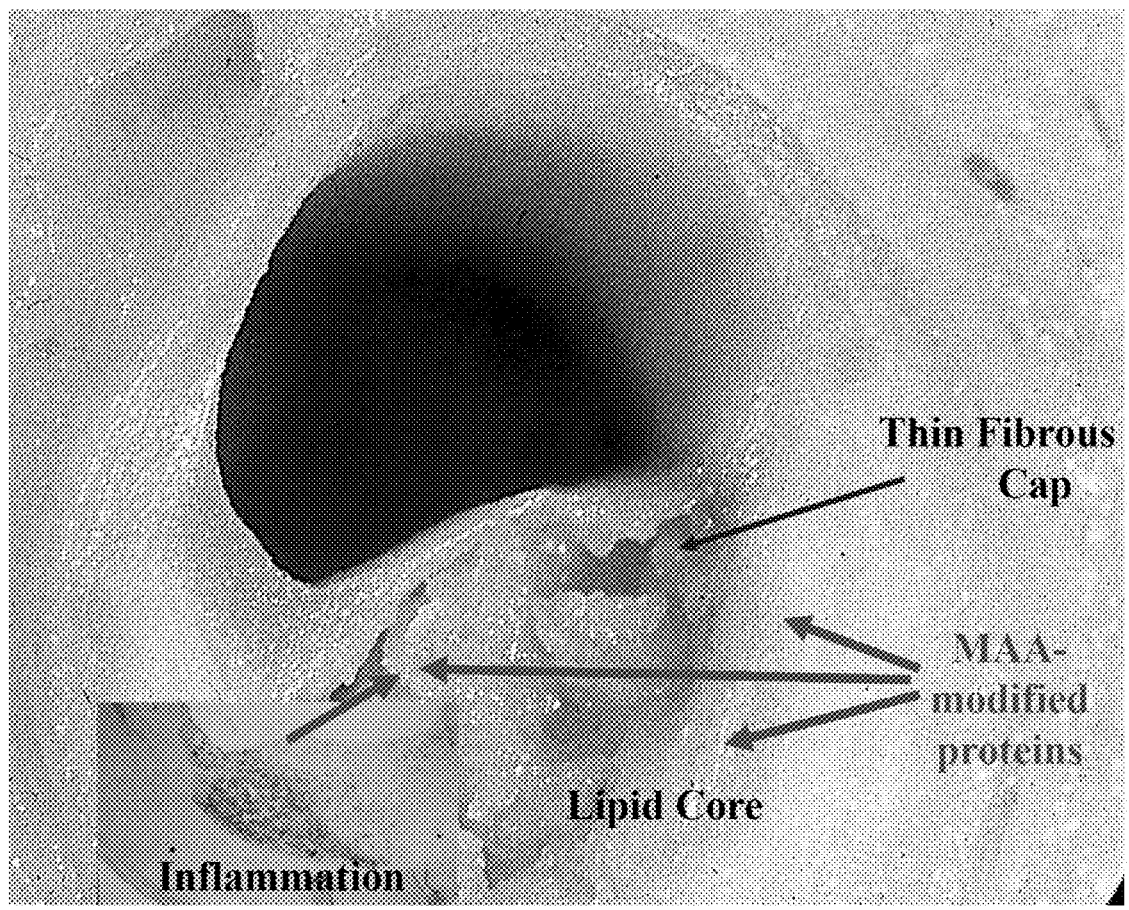
FIG. 8 shows an illustration of a vulnerable plaque.

FIG. 8 provides an illustration of vulnerable plaque showing the lipid core, site of inflammation, thin fibrous cap, and location of MAA modified proteins (MAA adduct).

Figure 9:
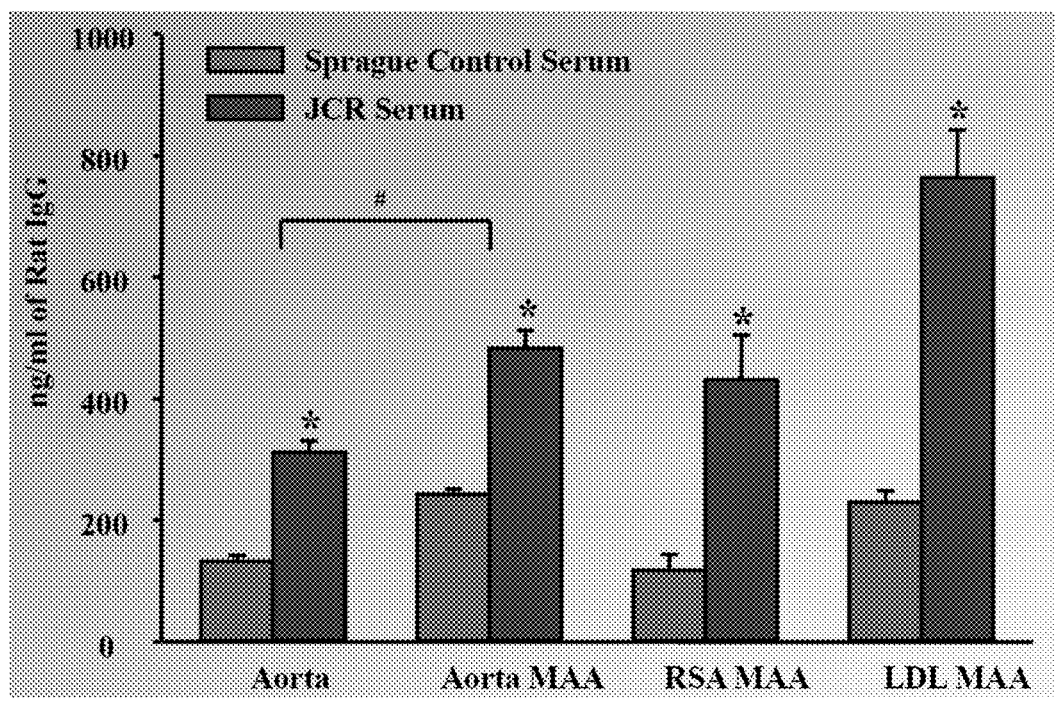
FIG. 9 illustrates serum antibody concentrations to MAA-modified rat albumin in JCR rats. Data are expressed as the means±SEM of six animal experiments. *P≤0.004, significantly increased compared to Sprague control serum. #P≤0.001, significantly different comparing aorta to aorta MAA coating antigens.

In another study, serum antibody concentrations to MAA-modified rat albumin was determined in JCR rats. JCR rats were fed a high-cholesterol diet for 6-8 months. Serum was assayed for the presence of antibody to rat serum albumin modified with MAA (RSA-MAA), normal rat serum albumin (RSA), or aorta and aorta modified with MAA. The data are shown in FIG. 9. The difference between the activity on unmodified proteins minus MAA-modified proteins is expressed in ng/ml of rat IgG extrapolated from a standard curve.

Figure 10:
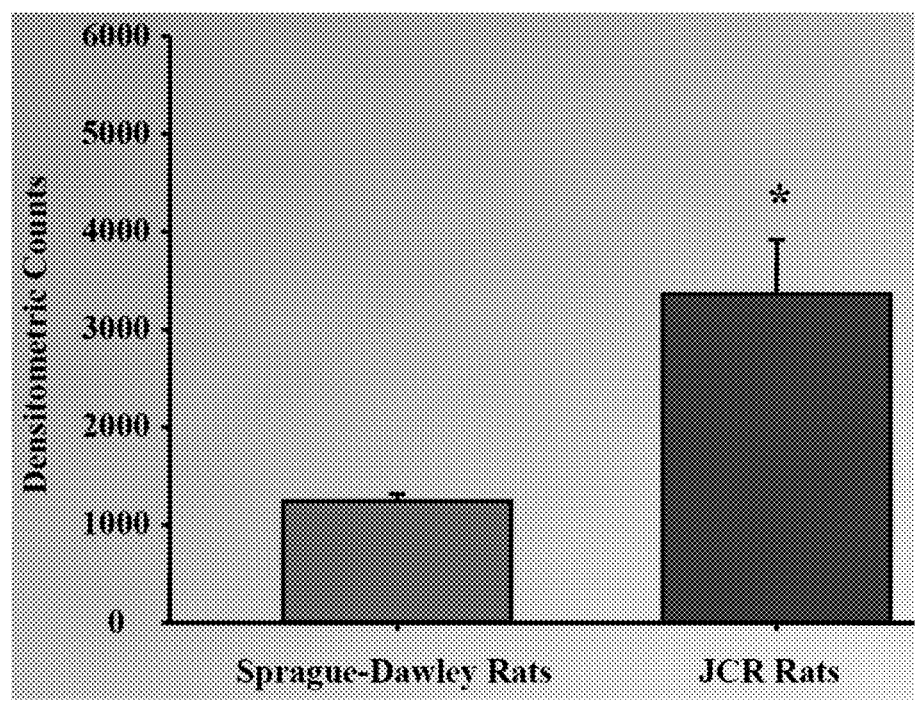
FIG. 10 illustrates immunoprecipitation of MAA modified proteins from aortic tissues of JCR rats. Data represent the intensity of staining 88-kDa of an 88 band expressed as the means±SEM of three animal experiments *P=0.005, significantly different from Sprague control rats.

Immunoprecipitation of MAA modified proteins (MAA protein adduct) from aortic tissue of JCR rates was also performed. JCR rats were fed a high cholesterol diet for 6-8 months. Aortic tissue from JCR or Sprague-Dawley rats was collected and immuno-precipitated using a monoclonal anti-MAA antibody. Proteins were resolved by SDS-PAGE and probed with a rabbit anti-MAA antibody by Western blot. The results are shown in FIG. 10. Data represent the intensity of staining 88-kDa of an 88 band expressed as the means±SEM of three animal experiments. The JCR rats shows significantly higher levels of MAA adduct.

This model appears to mimic the human system with respect to: 1) Developing atherosclerotic plaques; 2) Developing antibody titers to MAA-modified proteins; and 3) The formation of MAA modified proteins can be detected in the aortas of JCR rats that developed atherosclerosis.

Without being bound to a particular theory, it is believed that in the progression of atherosclerosis and in particular coronary artery disease, a site of inflammation is set up wherein oxidized proteins and LDL bind, internalize and initiate pro-inflammatory responses. Some of the oxLDL and MAA modified proteins are released from the site and migrate to the immune system to initiate immune responses in a load dependent process. Antibody is initiated that correlates with the development of an atherosclerotic plaque as well as its progression. The more antibody to MAA, the greater the chance the plaque is unstable. As the oxLDL and adducted proteins accumulate more inflammatory cells accumulate, infiltrate and the plaque grows causing angina. Eventually, the inflammation becomes overwhelming causing thinning of the fibrous plaque cap due to cytokines and immune reactions), and antibody concentrations increase due to leaky membranes and in response to the leaked modified macromolecules. Eventually the plaque rupture causes the release of large amounts of oxLDL and MAA-modified proteins that binds the circulating antibody resulting in decreased antibody concentrations.

Example 3

Increased MAA-Protein Adducts and Anti-MAA Antibodies in Patients with Atherosclerotic Disease and Acute Myocardial Infarction: New Biomarkers for the Assessment of the Vulnerable Plaque Oxidized proteins have been implicated in the development and progression of atherosclerosis. Malondialdehyde/Acetaldehyde (MAA) modified LDL is highly oxidized and a dominate epitope formed following the modification of proteins with malondialdehyde. MAA modified proteins also bind scavenger receptors on endothelial cells and macrophages and promote the release of pro-inflammatory cytokines. MAA modified proteins have been detected in a JCR rat model of atherosclerosis.

Objective:

The purpose of this study was to evaluate tissue from patients with atherosclerosis for the presence of MAA adducted proteins, and determine the level of circulating anti-MAA antibodies in these patients.

Methods:

Serum samples from normal controls (N=82), stable angina (N=42), acute myocardial infarction (AMI) (N=39), and coronary artery bypass graph surgery (CABG) (N=72) were collected and tested for the presence of circulating MAA modified proteins and anti-MAA antibodies. Aortic punch biopsies from CABG patients were subjected to immunohistochemical staining using a monoclonal mouse anti-MAA antibody and detection by confocal microscopy.

Results:

Circulating antibodies to MAA modified proteins in serum from patients with stable angina, acute MI, and CABG were significantly increased compared to normal healthy controls P<0.001. Serum samples from patients with acute MI had significantly increased levels of circulating anti-MAA antibodies compared to serum samples from stable angina P<0.04 or CABG P<0.004 patients. Confocal microscopy of aortic punch biopsies showed an increased level of the MAA-adduct.

Conclusions

The significantly lower levels of anti-MAA antibody in AMI patients are believed to be a result of an initial increase in antibody production during the acute phase with a subsequent decrease as modified proteins or LDL are cleared following medical stabilization of the patient prior to stent or bypass surgery. These data show a significant increase in the levels of circulating anti-MAA antibodies, and the presence of MAA adducts in the tissues of patients with atherosclerosis. Anti-MAA antibodies and MAA modified proteins can serve as additional biomarkers of atherosclerotic disease and the assessment of the vulnerable plaque.

Example 4

Antibody Isotypes to MAA in CAD

Figure 11:
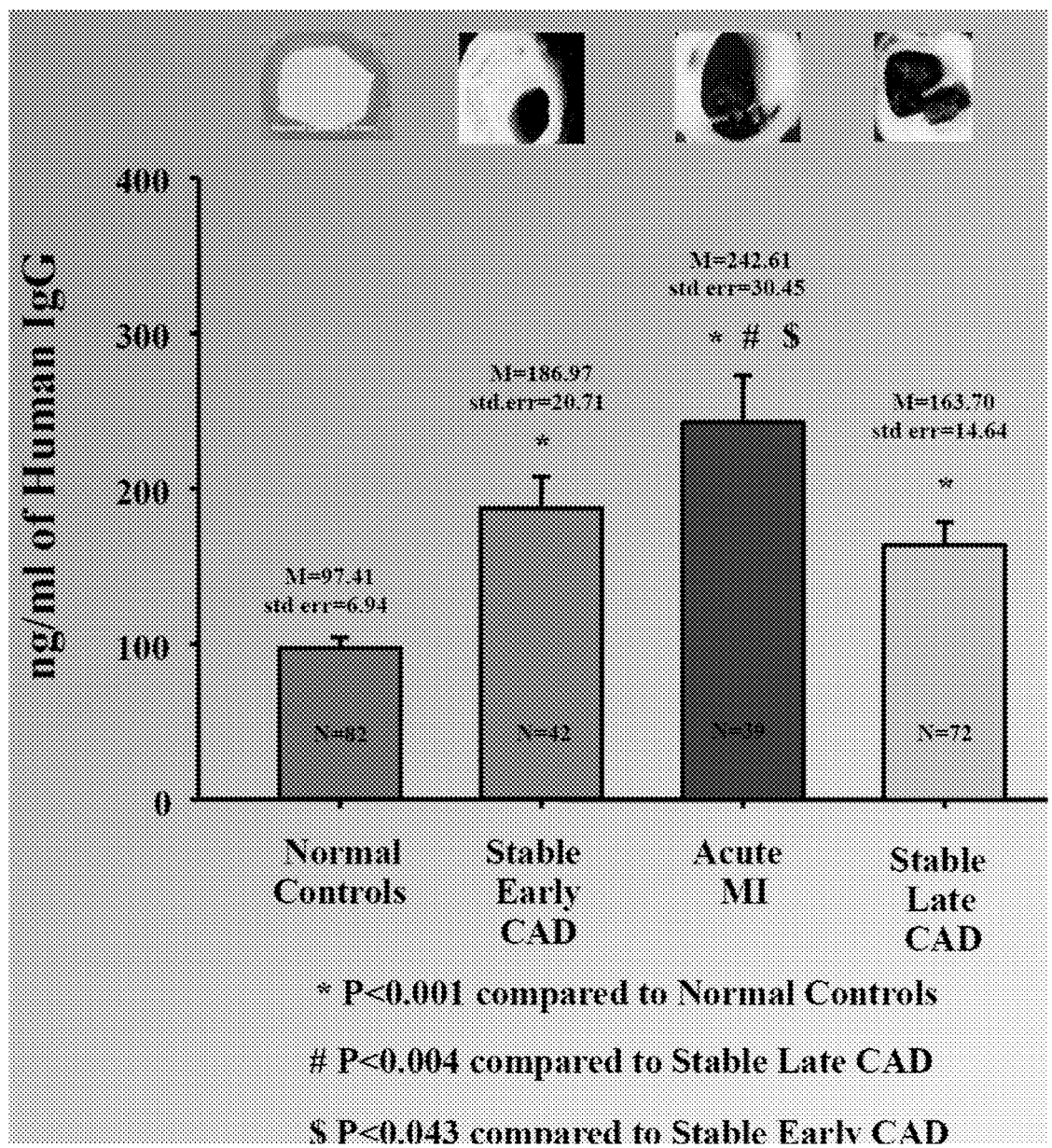
FIG. 11 shows serum concentration of IgG antibody to MAA in normal controls as compared to individuals with known coronary artery disease (CAD).

Serum concentration of different antibody isotypes (IgG, IgM, and IgA) to MAA adducts in sera from normal controls, acute MI patients, stable early CAD patients, and stable late CAD patients were determined. As shown in FIG. 11, patients with acute MI had significantly higher levels of IgG to MAA adducts as compared to normal controls or to patients with stable early CAD or stable late stage CAD.

Figure 12:
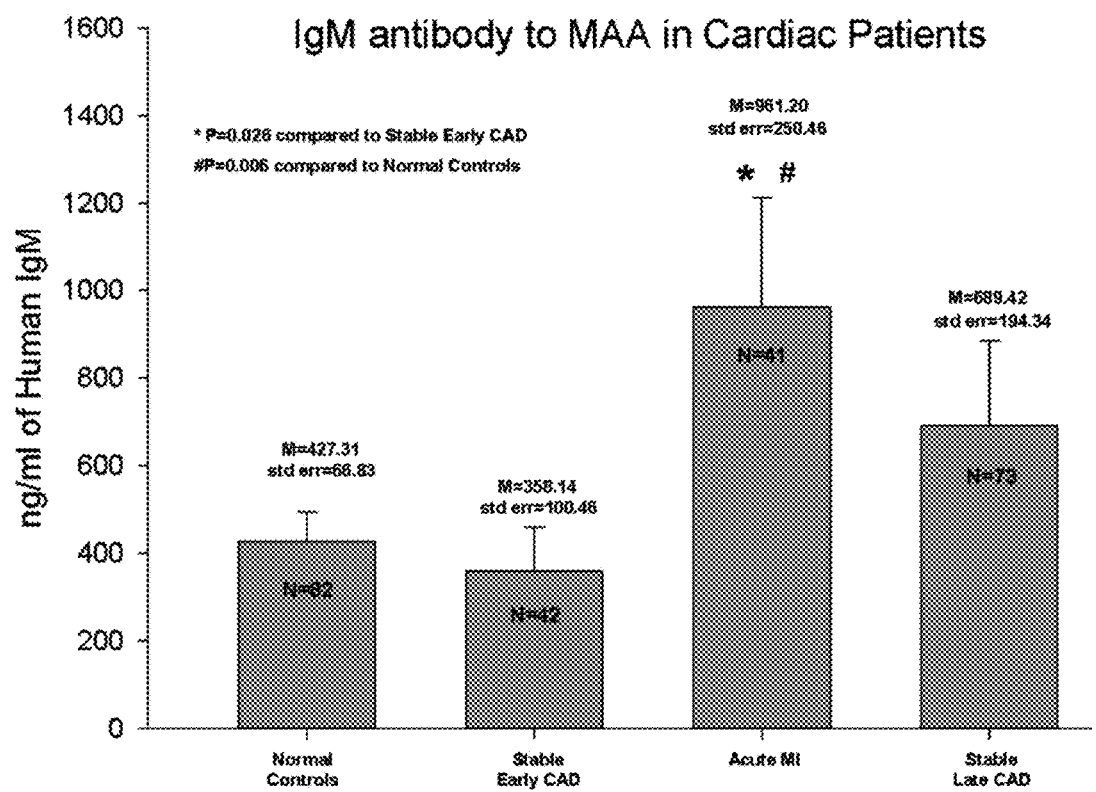
FIG. 12 shows serum concentration of IgM antibody to MAA in normal controls as compared to individuals with known coronary artery disease (CAD).

As shown in FIG. 12, patients with an Acute MI had significantly higher IgM levels of antibody to MAA adduct as compared to normal controls and to patients with stable early CAD or stable late CAD. These findings closely mimic those observed for IgG antibodies to MAA adducts.

Figure 13:
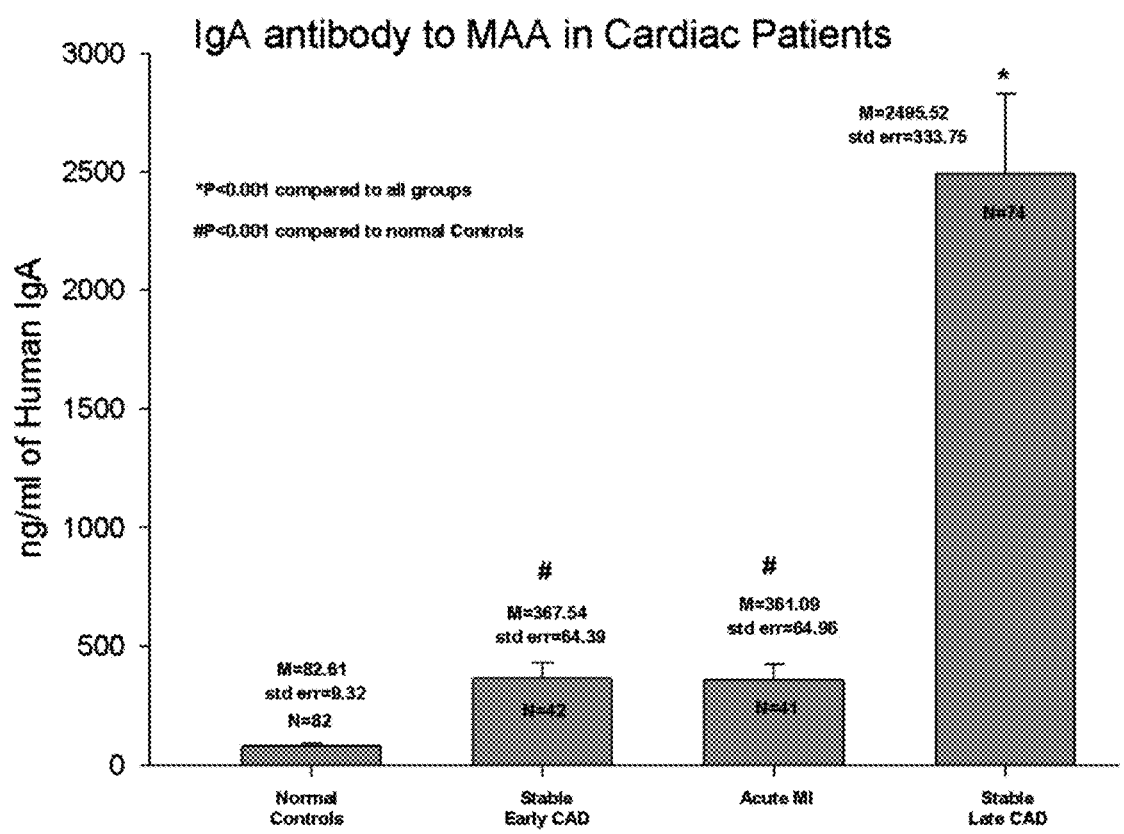
FIG. 13 shows serum concentration of IgA antibody to MAA adducts in normal controls as compared to individuals with known coronary artery disease (CAD).

FIG. 13 shows that serum from patients with stable late CAD higher had significantly levels of IgA antibody to MAA adducts as compared to normal controls or to patients with stable early CAD and stable late CAD. Patients with Stable Early CAD and acute MI also had significantly higher levels of IgA antibody to MAA adduct than normal controls.

Without being bound to a particular theory, it is believed that during the progression of atherosclerosis, and in particular coronary artery disease, a site of inflammation is set up wherein oxidized proteins and LDL bind, internalize and initiate pro-inflammatory responses. Some oxLDL and MAA modified proteins are released from the site and migrate to the immune system to initiate immune responses in a load-dependent process, resulting in the production of IgM antibodies. As the oxLDL and adducted proteins accumulate, more inflammatory cells infiltrate and the plaque grows causing angina. Eventually, the inflammation becomes overwhelming the IgM antibody is class switched to the more pathogenic IgG antibody that aids in the thinning of the fibrous plaque cap (due to due to cytokines and immune reactions reactions), and antibody concentrations increase due to leaky membranes and in response to the increased levels of leaked modified macromolecules. Eventually the plaque ruptures causes the release of large amounts of oxLDL and MAA-modified modified proteins and acute myocardial infarction. Alternatively, in patients with stable CAD, the oxLDL and adducted proteins accumulate on the adventitial side of the cap (not in the lumen of the vasculature) and the inflammatory response is decreased. The cytokines released result in an IgA response that is less pathogenic and the fibrous plaque cap is left intact, resulting in a stable CAD.

Example 5

Differentiating Normal Coronary Arteries, Stable Atheromatous Lesions and Unstable Atheromatous Lesions: MAA-Protein Adducts and Anti-MAA Antibodies Isotypes in Patients with Atherosclerotic Disease and Acute Myocardial Infarction Oxidized proteins have been implicated in the development and progression of atherosclerosis. Malondialdehyde (MDA)-acetaldehyde (AA) adduct (MAA), is produced and is the dominant epitope formed following incubation of proteins with the oxidative product MDA. Additionally, these MAA-modified proteins have been detected in JCR atherosclerotic rat aortic tissue and the human model of atherosclerosis. MAA-modified proteins have been implicated in the progression of atherosclerotic disease.

Objective:

The purpose of this study was to evaluate the association of MAA-adducted proteins and circulating IgM, IgG and IgA anti-MAA antibody isotypes to patients with normal coronary arteries and patients with stable and unstable atherosclerotic lesions.

Methods:

Over a six-month period, serum samples from normal controls (n=82), stable angina (n=42), acute myocardial infarction (AMI) (n=41), and coronary artery bypass graph surgery (CABG) (n=72) patients were collected and tested for the presence of anti-MAA antibody isotypes. All samples were collected prior to heparinization, intervention and/or bypass pump initiation. Aortic punch biopsies from CABG patients were subjected to immunohistochemical (IHC) staining using a monoclonal mouse anti-MAA antibody and detection by confocal microscopy.

Results:

Normal control patients had a significantly lower circulating anti-MAA IgG (97 ng/ml, SE=6.9) and IgA (82 ng/ml) as compared to patients with coronary artery disease ($p<0.001$). AMI patients had a significantly increased level of circulating anti-MAA IgG antibodies (242 ng/ml, SE=30.5) compared to stable angina (186 ng/ml, SE=20.7) ($p<0.04$) or CABG patients (163 ng/ml, SE=14.6) ($p<0.004$). Serum samples from patients with CABG had significantly increased levels of circulating anti-MAA IgA antibodies (2495 ng/ml, SE=334) compared to stable angina (367 ng/ml, SE=64.4) ($p<0.001$) or AMI patients (361 ng/ml, SE=65.0) ($p<0.001$). Anti-MAA IgM antibodies were significantly different across the groups in similar fashion to IgG results. Confocal microscopy of aortic punch biopsies confirms an increased level of the MAA-adducts within the interstitial spaces of the aorta media.

Conclusions

These data show that MAA-modified proteins are present in atherosclerotic tissues and there is a significant increase in the levels of circulating anti-MAA antibodies (IgM, IgG and IgA) in patients with coronary artery disease. Anti-MAA IgM and IgG phenotypes are significantly increased in patients who present with an AMI compared to normal coronary artery and stable CAD patients, whereas, the anti-MAA IgA phenotype is significantly increased in patients who present for CABG compared to all other groups. The immunoglobulin phenotype (IgM, IgG and/or IgA) is hypothesized secondary to differences in antigenic sensitization ($Th_1$ vs. $Th_2$) of MAA-modified proteins in diseased tissue.

Implications:

Anti-MAA IgM, IgG and IgA antibody isotypes and MAA-modified proteins can serve as biomarkers for subclinical atherosclerotic disease (IgM, IgG and IgA) as well as differentiate CAD patients who have stable (IgA) and unstable (IgG) atherosclerotic plaques.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A kit for evaluating the presence of and/or prognosis for atherosclerosis in a mammal, said kit comprising packaging containing:
   a malondialdehyde-acetaldehyde (MAA) protein adduct;
   an anti-IgG antibody capable of specifically binding to IgG antibodies when said IgG antibodies are bound to said MAA protein adduct;
   an anti-IgM antibody capable of specifically binding to IgM antibodies when said IgM antibodies are bound to said MAA protein adduct; and
   an anti-IgA antibody capable of specifically binding to IgA antibodies when said IgA antibodies are bound to said MAA protein adduct.

2. The kit of claim 1, wherein said MAA protein adduct is provided immobilized on a solid support.

3. The kit of claim 2, wherein said solid support comprises a material selected from the group consisting of a plastic, glass, quartz, a gel, and a metal.

4. The kit of claim 2, wherein said solid support is selected from the group consisting of a particle, a test strip, a microtiter plate, an ELISA plate, and a microfluidic channel or chamber.

5. The kit of claim 1, further comprising instructional materials that teach the use of measurement of antibodies against a MAA protein adduct to evaluate the risk for an adverse cardiac event, and/or to determine the prognosis of a mammal, and/or to evaluate the progression of atherosclerosis in a mammal, and/or to evaluate a treatment regimen.

* * * * *